(12) United States Patent
Thomas et al.

(10) Patent No.: US 12,140,534 B2
(45) Date of Patent: *Nov. 12, 2024

(54) DEVICES, METHODS, AND SYSTEMS FOR DERIVING A PERMEATE FROM A FEED SOLUTION

(71) Applicant: Sequitur Health Corp., Scottsdale, AZ (US)

(72) Inventors: Marylaura L. Thomas, Scottsdale, AZ (US); Leslie F. Thomas, Scottsdale, AZ (US); Erica S. Forzani, Phoenix, AZ (US); Phuoc H. H. Duong, Phoenix, AZ (US)

(73) Assignee: Sequitur Health Corp., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/093,469

(22) Filed: Jan. 5, 2023

(65) Prior Publication Data
US 2024/0230522 A1 Jul. 11, 2024

(51) Int. Cl.
| G01N 21/31 | (2006.01) |
| G01N 1/22 | (2006.01) |
| G01N 1/44 | (2006.01) |
| G01N 33/49 | (2006.01) |

(52) U.S. Cl.
CPC ......... *G01N 21/31* (2013.01); *G01N 1/2205* (2013.01); *G01N 1/44* (2013.01); *G01N 33/4925* (2013.01); *G01N 2201/062* (2013.01)

(58) Field of Classification Search
CPC ........ G01N 21/31; G01N 1/2205; G01N 1/44; G01N 33/4925; G01N 2201/062
See application file for complete search history.

(56) References Cited

U.S. PATENT DOCUMENTS

| 4,066,403 A | 1/1978 | Bruschi |
| 4,144,306 A | 3/1979 | Figueras |
| 4,430,420 A | 2/1984 | Adin |
| 4,436,631 A | 3/1984 | Graham, Jr. et al. |
| 4,548,906 A | 10/1985 | Sekikawa et al. |
| 4,719,085 A | 1/1988 | Jacobs |
| 4,816,224 A | 3/1989 | Vogel et al. |

(Continued)

FOREIGN PATENT DOCUMENTS

| DE | 102011110638 | 2/2013 |
| DE | 202014002369 U1 | 6/2014 |

(Continued)

OTHER PUBLICATIONS

Ayyub et al.; "Simple and inexpensive quantification of ammonia in whole blood"; Molecula Genetics and Metabolism 115 (2015); Apr. 25, 2015; pp. 95-100.

(Continued)

*Primary Examiner* — Jamil Ahmed
(74) *Attorney, Agent, or Firm* — LOZA & LOZA, LLP; David S. Sarisky

(57) ABSTRACT

A device, e.g., sensing cartridge, includes a first member and a second member coupled to the first member. The first member is configured to separate a component from a feed solution, where the component has a hydrodynamic diameter greater than 0.01 micrometers (μm). The second member is configured to wick a permeate from the first member.

16 Claims, 22 Drawing Sheets

(56) References Cited

U.S. PATENT DOCUMENTS

| | | | |
|---|---|---|---|
| 5,008,078 A | 4/1991 | Yaginuma et al. | |
| 5,082,516 A | 1/1992 | Akao et al. | |
| 5,141,850 A | 8/1992 | Cole et al. | |
| 5,183,763 A | 2/1993 | Mallow et al. | |
| 5,198,335 A * | 3/1993 | Sekikawa | C12Q 1/32 |
| | | | 422/417 |
| 5,240,862 A * | 8/1993 | Koenhen | B01L 3/5023 |
| | | | 210/500.24 |
| 5,258,163 A | 11/1993 | Krause et al. | |
| 5,286,624 A | 2/1994 | Terashima et al. | |
| 5,597,532 A | 1/1997 | Connolly | |
| 5,702,884 A | 12/1997 | Ekeze et al. | |
| 5,906,742 A | 5/1999 | Wang et al. | |
| 5,919,711 A | 7/1999 | Boyd et al. | |
| 6,045,899 A | 4/2000 | Wang et al. | |
| 6,069,014 A * | 5/2000 | Schrier | G01N 33/521 |
| | | | 436/514 |
| 6,106,732 A | 8/2000 | Johnston et al. | |
| 6,383,818 B1 | 5/2002 | Arai et al. | |
| 6,844,149 B2 | 1/2005 | Goldman | |
| 7,087,397 B2 | 8/2006 | Anaokar et al. | |
| 7,125,493 B2 | 10/2006 | Wang et al. | |
| 7,625,721 B2 | 12/2009 | Lawrence et al. | |
| 8,307,531 B2 | 11/2012 | Lawrence | |
| 8,409,864 B2 | 4/2013 | Ash | |
| 8,440,085 B2 | 5/2013 | Bormann et al. | |
| 9,068,997 B2 | 6/2015 | Pettigrew et al. | |
| 9,341,504 B2 | 5/2016 | Lochhead et al. | |
| 9,625,443 B2 | 4/2017 | Veltman et al. | |
| 9,835,613 B2 | 12/2017 | Veltman et al. | |
| 9,952,199 B2 | 4/2018 | Ayyub et al. | |
| 10,022,081 B2 | 7/2018 | Künnecke | |
| 10,151,743 B2 | 12/2018 | Veltman et al. | |
| 10,384,206 B2 | 8/2019 | Longenbach et al. | |
| 10,578,616 B2 | 3/2020 | Kamei et al. | |
| 10,620,187 B2 | 4/2020 | Ayyub et al. | |
| 10,663,379 B2 | 5/2020 | Dick et al. | |
| 10,731,200 B2 | 8/2020 | Funamoto et al. | |
| 10,765,793 B1 | 9/2020 | Mallipalli et al. | |
| 10,777,402 B2 | 9/2020 | Ouyang et al. | |
| 2002/0117639 A1 | 8/2002 | Paolini et al. | |
| 2003/0212344 A1 | 11/2003 | Yuzhakov et al. | |
| 2005/0120775 A1 | 6/2005 | Grayfer et al. | |
| 2007/0151924 A1* | 7/2007 | Mir | B01D 63/08 |
| | | | 210/321.88 |
| 2007/0244368 A1 | 10/2007 | Bayloff et al. | |
| 2008/0138890 A1 | 6/2008 | Horiike et al. | |
| 2009/0311575 A1 | 12/2009 | Babcock | |
| 2012/0067744 A1 | 3/2012 | Vincent | |
| 2012/0181184 A1* | 7/2012 | Whitesides | B01L 3/502 |
| | | | 204/400 |
| 2012/0198684 A1 | 8/2012 | Carrilho et al. | |
| 2013/0283931 A1 | 10/2013 | Lochhead et al. | |
| 2015/0125882 A1 | 5/2015 | Bornheimer et al. | |
| 2015/0266023 A1 | 9/2015 | Fuchiwaki et al. | |
| 2016/0051980 A1 | 2/2016 | Hong et al. | |
| 2016/0096148 A1 | 4/2016 | Schuetz et al. | |
| 2016/0290901 A1 | 10/2016 | Dick et al. | |
| 2017/0023446 A1 | 1/2017 | Rietveld et al. | |
| 2017/0082605 A1 | 3/2017 | Veltman et al. | |
| 2018/0037927 A1 | 2/2018 | Katsuki et al. | |
| 2018/0112250 A1 | 4/2018 | Funamoto et al. | |
| 2020/0174025 A1 | 6/2020 | Joyce | |
| 2021/0007885 A1* | 1/2021 | Chirico | B32B 27/365 |
| 2021/0076999 A1* | 3/2021 | Thomas | A61B 5/14552 |
| 2021/0148906 A1 | 5/2021 | Fiechtner et al. | |

FOREIGN PATENT DOCUMENTS

| | | |
|---|---|---|
| DE | 102015012519 A1 | 3/2017 |
| JP | S58193459 A | 11/1983 |
| JP | H0616033 B2 | 3/1994 |
| JP | 2010038666 A | 2/2010 |
| JP | 2016529515 A | 9/2016 |
| KR | 20200035702 A | 4/2020 |
| KR | 20220166132 | 12/2022 |
| WO | 1995032414 | 11/1995 |
| WO | 2021188594 A1 | 9/2021 |

OTHER PUBLICATIONS

Ayyub et al.; "Time-dependent negative bias in plasma ammonia samples in a clinical setting"; Clinica Chimica Acta 471 (2017); May 9, 2017; pp. 126-127.

Cuhadar et al.; "Detection of preanalytical errors in arterial blood gas analysis"; Coation Society of Medical Biochemistry and Laboratory Medicin; Mar. 15, 2022; 9 pages.

Laakman et al.; "Data on the clinical, analytical, and laboratory factors associated with negative anion gaps at an academic medical center"; Elsevier Inc.; Jun. 2, 2022; 12 pages.

Ray et al.; "Urea recovery from fresh human urine by forward osmosis and membrane distillation (FO-MD)"; Environmental Science Water Research & Technology; The Royal Society of Chemistry; Aug. 31, 2019; pp. 1993-2003.

Ray et al.; "Rejection of nitrogen species in real fresh and hydrolyzed human urine by reverse osmosis and nanofiltration"; Journal of Environmental Chemical Engineering 8 (2020); Apr. 23, 2020; 9 pages.

Ray et al.; "Ammonia Recovery from Hydrolyzed Human Urine by Forward Osmosis with Acidified Draw Solution"; ACS Publications; American Chemical Society; Aug. 7, 2020; 10 pages.

Ray et al.; "Ammonia recovery and fouling mitigation of hydrolyzed human urine treated by nanofiltration and reverse osmosis"; Environmental Science Water Research & Technology; The Royal Society of Chemistry; Dec. 29, 2021; 14 pages.

"Rochester 2022 Test Catalog"; Mayo Clinic Laboratories; Aug. 8, 2022; 1370 pages.

Srivastava et al.; "Basic overview of human physiology"; Smart Healthcare for Disease Diagnosis and Prevention; 2020; pp. 193-212.

Trulock, III; "Arterial Blood Gases"; The Pulmonary System; pp. 254-257.

Veltman et al.; "Point-of-Care Analysis of Blood Ammonia with a Gas-Phase Sensor"; ACS Publications; American Chemical Society. Jun. 15, 2020; 7 pages.

Veltman; "Point-of-Care Ammonia Monitoring from a Single Drop of Blood"; OAA Newsletter; Fall 2020; https://www.paanews.org/new-point-of-care-ammonia-monitoring.html; 4 pages.

Non-Final Office Action on co-pending (U.S. Appl. No. 18/093,466) dated Apr. 6, 2023.

Final Office Action on co-pending (U.S. Appl. No. 18/093,466) dated Oct. 17, 2023.

Interntional Search Report and Written Opinion, PCT/US2024/010035, Apr. 25, 2024, 9 pgs.

Notice of Allowance on co-pending U.S. application (U.S. Appl. No. 18/093,466) dated May 30, 2024.

Non-Final Office Action on co-pending U.S. application (U.S. Appl. No. 18/093,466) dated Mar. 6, 2024.

* cited by examiner

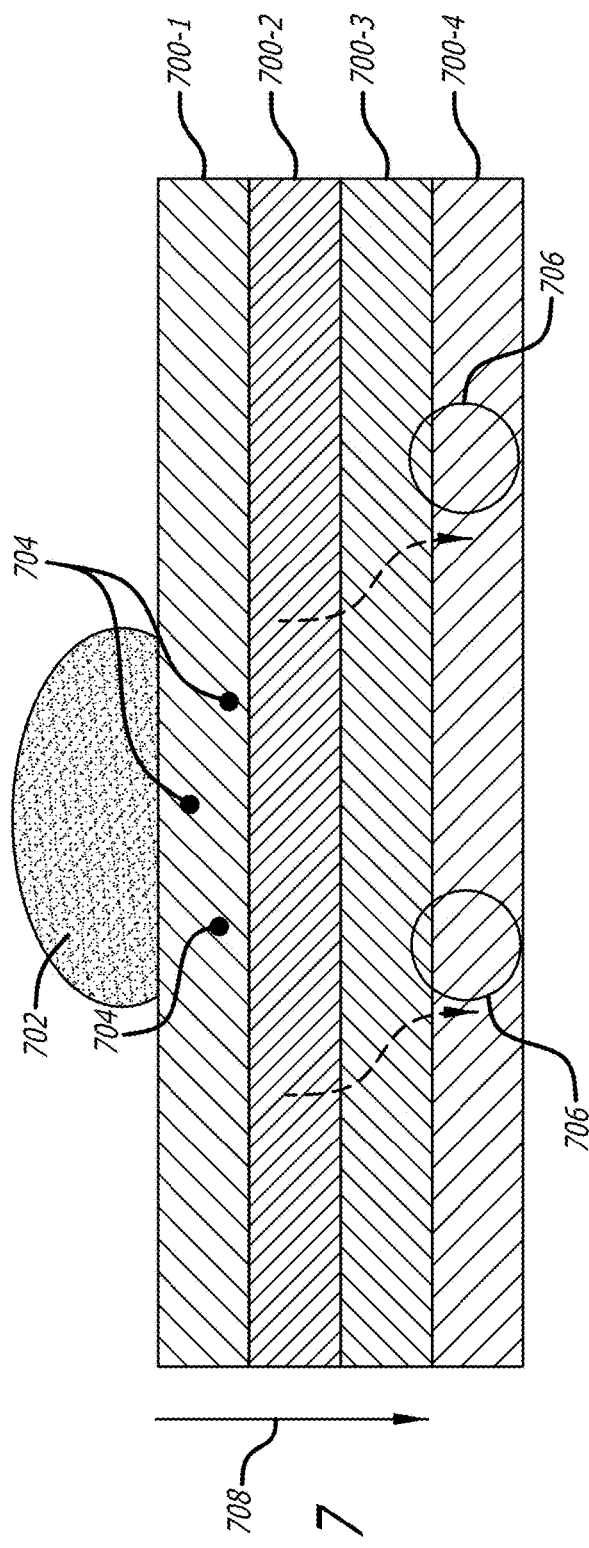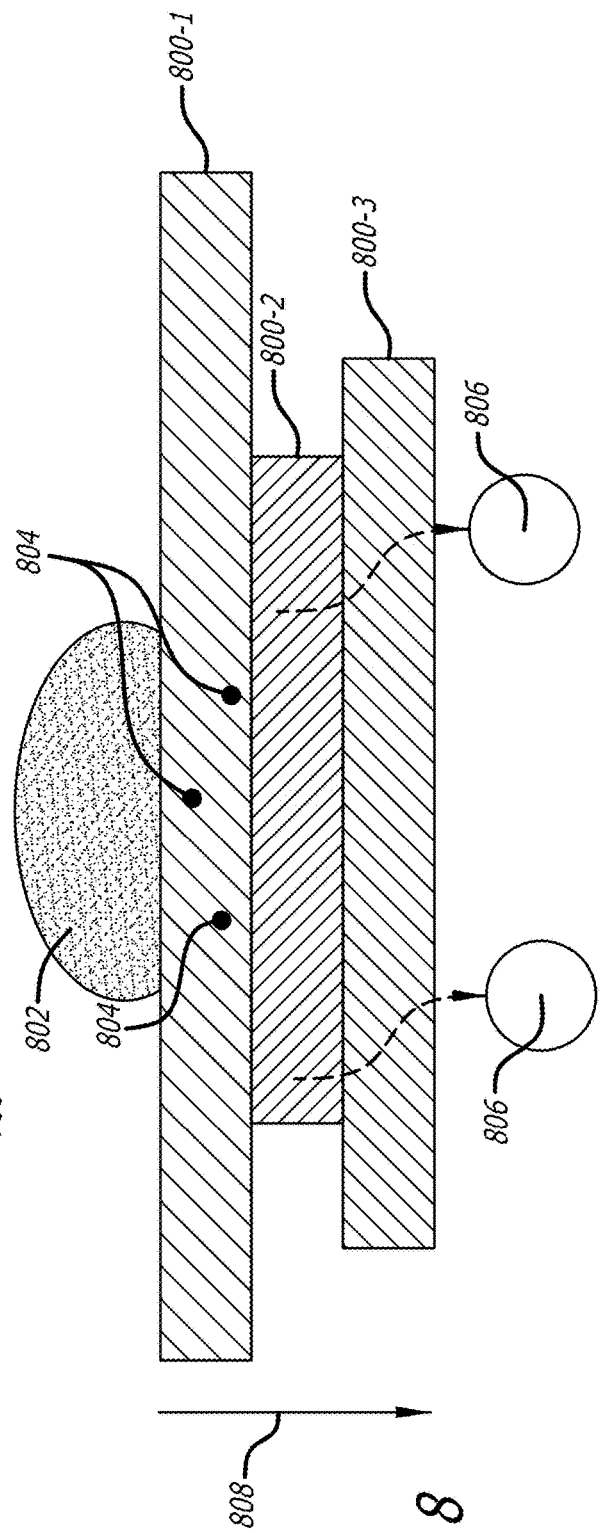

|  | 1 | 2 | 3 | 4 | 5 | 6 |
|---|---|---|---|---|---|---|
| Nylon |  | 0.45 | 48.5 | 2.6 | 53.3 | 3.9 |
| Nylon |  | 5 | 0.8 | 1.0 | 2.0 | 2.2 |
| Nylon |  | 140 | 3.5 | 2.1 | 0.5 | 1.9 |
| Alumina |  | 0.5 | 22.8 | 15.5 | 33.3 | 4.2 |
| Silica |  |  | 48.5 | 7.0 | 64.3 | 3.6 |
| Cotton linter |  |  | 27.3 | 7.4 | 44.8 | 1.9 |
| Cotton linter |  |  | 29.0 | 6.2 | 57.5 | 5.7 |
| Cellulose |  | 11 | 24.3 | 4.3 | 32.3 | 3.2 |
| Cellulose |  | 6 | 31.5 | 3.1 | 68.5 | 3.9 |
| Cellulose |  | 8 | 20.8 | 1.3 | 43.3 | 3.3 |
| Cellulose |  | 22 | 22.0 | 5.0 | 39.3 | 2.5 |
| Cellulose |  | 2.5 | 30.8 | 2.8 | 48.5 | 0.6 |
| Cellulose |  | 16 | 29.8 | 5.7 | 40.8 | 3.4 |
| Cellulose |  | 3 | 26.8 | 2.6 | 31.3 | 2.2 |
| Cellulose |  | 10 | 18.3 | 1.7 | 47.8 | 15.9 |
| latex-bound glass fiber |  | 2.3 | 0.5 | 1.0 | 2.5 | 0.7 |
| Polyvinyl alcohol-bound glass fiber |  |  | 2.0 | 4.5 | 32.5 | 9.2 |
| borosilicate glass |  | 1.2 | 35.3 | 5.5 | 70.8 | 2.6 |
| glass fiber |  |  | 34.5 | 8.1 | 30.5 | 4.2 |
| glass fiber |  |  | 25.3 | 5.1 | 39.0 | 4.5 |
| glass fiber |  | 3.1 | 2.0 | 3.5 | 54.0 | 10.7 |
| glass fiber |  | 0.7 | 33.0 | 7.7 | 75.5 | 5.7 |
| bound glass fiber |  |  | 13.3 | 2.6 | 65.3 | 31.4 |
| bound glass fiber |  |  | 0.0 | 2.2 | 20.5 | 12.0 |
| bound glass fiber |  |  | 2.3 | 1.2 | 32.3 | 5.6 |
| fiber |  |  | 27.8 | 5.1 | 43.3 | 4.2 |
| fiber |  |  | 30.3 | 5.3 | 58.3 | 2.2 |
| fiber |  |  | 38.5 | 3.0 | 70.0 | 0.8 |
| fiber |  |  | 6.0 | 3.3 | 29.0 | 9.2 |
| treated fiber |  |  | 10.3 | 7.8 | 26.3 | 4.9 |
| cellulose nitrate |  | 5 | 16.8 | 5.4 | 46.5 | 5.4 |
| cellulose nitrate |  | 12 | 1.5 | 2.9 | 19.0 | 2.0 |
| polyester backed polytetrafluoroethylene |  | 1 | -4.3 | 1.9 | -3.8 | 1.0 |
| polypropylene backed polytetrafluoroethylene |  | 1 | 1.0 | 2.8 | -3.3 | 1.3 |

FIG. 12

| 1 | 2 | 3 | 4 |
|---|---|---|---|
| Polytetrafluoroethylene | 0.2 | 25 | 130 |
| Polytetrafluoroethylene | 0.45 | 30 | 120 |
| Polytetrafluoroethylene | 1.0 | 200 | 700 |
| Polyvinylidene chloride | 0.45 | 100 | 525 |

| 1 | 2 |
|---|---|
| Erythrocytes | 7 |
| Leukocytes | 15 |
| thrombocytes | 3.6 |
| epithelial cells | 9 |
| sperm cells | 3.0 |
| neoplastic cells | 10.0 |
| lactocytes | No report |
| Breast milk stem cells | No report |
| Enterobacter cloacae | 0.5 |
| Enterococcus faecalis | 0.75 |
| Escherichia coli | 1.0 |
| Klebsiella pneumoniae | 1.0 |
| Proteus vulgaris | 1.0 |
| Pseudomonas aeruginosa | 1.0 |
| Salmonella | 1.25 |
| Shigella | 1.0 |
| Georgenia | 1.0 |
| Desulforhabdus | 2.0 |
| Thauera | 3.0 |
| Desulfuromonas | 1.5 |
| Arcobacter | 0.4 |

FIG. 23

| 1 | 2 | 3 |
|---|---|---|
| ammonium ($NH_4^+$) | alkaline medium | ammonia ($NH_3$) |
| bicarbonate ($HCO_3^-$) | acid medium | carbon dioxide ($CO_2$) |
| hemoglobin-bound to gases such as CO or cyanuric acid (HCN), or complexes with CO or HCN | lower pressure, higher temperature | CO, HCN |
| chloride ($Cl^-$) | two-step reaction catalyst (e.g; $Cu/O_2$) | chlorine ($Cl_2$) |
| proton ($H^+$) | reducing agent or hydrogenase | hydrogen ($H_2$) |
| phosphate ($PO_4^{3-}$) | acid medium/catalyst | diphosphorous pentaoxide ($P_2O_5$) |
| nitrate ($NO_3^-$), | acid medium/photolysis | nitrogen dioxide ($NO_2$) |
| nitrite ($NO_2^-$), | acid medium/catalyst | nitric oxide (NO) |
| arsenite ($AsO_3^{3-}$), | acid medium/catalyst | diarsenic trioxide ($As_2O_3$) |
| arsenate ($AsO_4^{3-}$), | acid medium/catalyst | diarsenic pentaoxide ($As_2O_5$) |
| sulfate ($SO_4^{2-}$). | acid medium/catalyst | sulfur dioxide ($SO_2$) |

DEVICES, METHODS, AND SYSTEMS FOR DERIVING A PERMEATE FROM A FEED SOLUTION

GOVERNMENT LICENSE RIGHTS

This invention was made with government support under Contract No. HD 107897 awarded by the National Institutes of Health. The government has certain rights in the invention.

TECHNICAL FIELD

The present disclosure relates generally to permeate derivation devices, and more particularly, to devices, methods, and systems for deriving a permeate from a feed solution for use in constituent measurement systems.

BACKGROUND

Measuring a constituent in a solution often involves multiple steps which may include separating a permeate from the solution and measuring the constituent from the permeate. The process of separating the permeate from the solution often introduces variabilities which may include variability in time and temperature during sample handling, sample collection procedures, laboratory environmental conditions, and individual patient status. Such variabilities often negatively impact constituent measurements by limiting accuracy and efficiency. Efforts to improve constituent measurements may include implementing multiple layers, chemical additives, and/or different derivation techniques in conventional permeate derivation devices. However, the multiple layers, the chemical additives, and/or the different derivation techniques may complicate constituent measurements as the conventional permeate derivation devices may not be able to accept certain solutions and/or may not be able to separate the permeate from the solutions. As such, there is a need for permeate derivation devices to efficiently separate a permeate from a solution while still providing accurate constituent measurements.

SUMMARY

In one aspect of the disclosure, a device for and a method of deriving a permeate from a feed solution are disclosed. A system for quantifying a constituent in a feed solution is also disclosed.

The device, e.g., sensing cartridge, for deriving a permeate from a feed solution includes a first member and a second member associated with or coupled to the first member. The first member is configured to separate a component from a feed solution, where the component has a hydrodynamic diameter greater than 0.01 micrometers ($\mu$m). The second member is configured to wick a permeate from the first member.

The method for deriving a permeate from a feed solution includes separating, by a first member, a component from the feed solution, where the component has a hydrodynamic diameter greater than 0.01 $\mu$m, and wicking, by a second member, the permeate from the first member.

The system for quantifying a constituent in a feed solution includes a sensing cartridge and a reader. The sensing cartridge includes a first member and a second member associated with or coupled to the first member. The first member is configured to separate a component from a feed solution, where the component has a hydrodynamic diameter greater than 0.01 $\mu$m. The second member is configured to wick a permeate from the first member and to shift a phase equilibrium of a constituent in the permeate to a gaseous state. The reader is configured to receive and removably couple with the sensing cartridge, and to quantify the constituent in the sensing cartridge based on at least one of optical sensing, electrochemical sensing, and electrical sensing.

Another system for quantifying a constituent in a feed solution includes a sensing cartridge, an optoelectronic reader, and a processor. The sensing cartridge includes a first member, a second member associated with or coupled to the first member, a third member associated with or coupled to the second member, and a fourth member associated with or coupled to the third member. The first member is configured to separate a component from a feed solution, where the component has a hydrodynamic diameter greater than 0.01 $\mu$m. The second member is configured to wick a permeate from the feed solution, where the second member acts on a constituent in the permeate to shift a phase equilibrium of the constituent to a gaseous state. The third member is configured to prevent liquid permeation produced by the shift in the phase equilibrium of the constituent to the gaseous state. The fourth member is configured to respond to diffused gas of the constituent. The optoelectronic reader includes a sensing light emitting diode (LED) configured to emit a light towards the sensing cartridge, and a sensing photodiode configured to sense reflected light from the sensing cartridge and to provide a measurement based on the reflected light. The processor is configured to quantify the constituent based on the measurement.

In another aspect of the disclosure, a device for and a method of deriving ammonia from whole blood are disclosed. A system for quantifying ammonia gas in whole blood is also disclosed.

The device, e.g., sensing cartridge, for deriving ammonia from whole blood includes a first member, a second member associated with or coupled to the first member, a third member associated with or coupled to the second member, and a fourth member associated with or coupled to the third member. The first member is configured to separate plasma from whole blood, where the whole blood has a cellular component with a hydrodynamic diameter greater than 0.01 $\mu$m. The second member is configured to wick the plasma from the whole blood, where the second member acts on ammonium in the plasma to shift a phase equilibrium of the ammonium to ammonia gas. The third member is configured to prevent liquid permeation produced by the shift in the phase equilibrium of the ammonium to the ammonia gas. The fourth member is configured to act on the ammonia gas.

The method for deriving ammonia from whole blood includes separating, by a first member, plasma from whole blood, where the whole blood has cellular components with a hydrodynamic diameter greater than 0.01 $\mu$m, and wicking, by a second member, the plasma from the whole blood, where the second member acts on ammonium in the plasma to shift a phase equilibrium of the ammonium to ammonia gas.

The system for quantifying ammonia in whole blood includes a sensing cartridge and a reader. The sensing cartridge includes a first member, a second member associated with or coupled to the first member, a third member associated with or coupled to the second member, and a fourth member associated with or coupled to the third member. The first member is configured to separate plasma from whole blood, where the whole blood has a cellular component with a hydrodynamic diameter greater than 0.01

μm. The second member is configured to wick the plasma from the whole blood, where the second member acts on ammonium in the plasma to shift a phase equilibrium of the ammonium to ammonia gas. The third member is configured to prevent liquid permeation produced by the shift in the phase equilibrium of the ammonium to the ammonia gas. The fourth member is configured to act on the ammonia gas. The reader is configured to receive and removably couple with the sensing cartridge, and to quantify the ammonia gas in the sensing cartridge based on at least one of optical sensing, electrochemical sensing, and electrical sensing.

Another system for quantifying ammonia in whole blood includes a sensing cartridge, an optoelectronic reader, and a processor. The sensing cartridge includes a first member, a second member associated with or coupled to the first member, a third member associated with or coupled to the second member, and a fourth member associated with or coupled to the third member. The first member is configured to separate plasma from whole blood, where the whole blood has a cellular component with a hydrodynamic diameter greater than 0.01 μm. The second member is configured to wick the plasma from the whole blood, where the second member acts on ammonium in the plasma to shift a phase equilibrium of the ammonium to ammonia gas. The third member is configured to prevent liquid permeation produced by the shift in the phase equilibrium of the ammonium to the ammonia gas. The fourth member is configured to act on the ammonia gas. The optoelectronic reader includes a light emitting diode (LED) configured to emit a light towards the sensing cartridge, and a photodiode configured to sense reflected light from the sensing cartridge and to provide a measurement based on the reflected light. The processor is configured to quantify the ammonia gas based on the measurement.

In another aspect of the disclosure, a device for and a method of deriving ammonia from urine are disclosed. A system for quantifying ammonia gas in urine is also disclosed.

The device, e.g., sensing cartridge, for deriving ammonia from urine includes a first member, a second member associated with or coupled to the first member, a third member associated with or coupled to the second member, and a fourth member associated with or coupled to the third member. The first member is configured to separate supernatant from urine, where the urine has a cellular component with a hydrodynamic diameter greater than 0.01 μm. The second member is configured to wick the supernatant from the urine, where the second member acts on ammonium in the supernatant to shift a phase equilibrium of the ammonium to ammonia gas. The third member is configured to prevent liquid permeation produced by the shift in the phase equilibrium of the ammonium to the ammonia gas. The fourth member is configured to act on the ammonia gas.

The method for deriving ammonia from urine includes separating, by a first member, supernatant from urine, where the urine has cellular components with a hydrodynamic diameter greater than 0.01 μm, and wicking, by a second member, the supernatant from the urine, where the second member acts on ammonium in the supernatant to shift a phase equilibrium of the ammonium to ammonia gas.

The system for quantifying ammonia in urine includes a sensing cartridge and a reader. The sensing cartridge includes a first member, a second member associated with or coupled to the first member, a third member associated with or coupled to the second member, and a fourth member associated with or coupled to the third member. The first member is configured to separate supernatant from urine, where the urine has a cellular component with a hydrodynamic diameter greater than 0.01 μm. The second member is configured to wick the supernatant from the urine, where the second member acts on ammonium in the supernatant to shift a phase equilibrium of the ammonium to ammonia gas. The third member is configured to prevent liquid permeation produced by the shift in the phase equilibrium of the ammonium to the ammonia gas. The fourth member is configured to act on the ammonia gas. The reader is configured to receive and removably couple with the sensing cartridge, and to quantify the ammonia gas in the sensing cartridge based on at least one of optical sensing, electrochemical sensing, and electrical sensing.

Another system for quantifying ammonia in urine includes a sensing cartridge, an optoelectronic reader, and a processor. The sensing cartridge includes a first member, a second member associated with or coupled to the first member, a third member associated with or coupled to the second member, and a fourth member associated with or coupled to the third member. The first member is configured to separate supernatant from urine, where the urine has a cellular component with a hydrodynamic diameter greater than 0.01 μm. The second member is configured to wick the supernatant from the urine, where the second member acts on ammonium in the supernatant to shift a phase equilibrium of the ammonium to ammonia gas. The third member is configured to prevent liquid permeation produced by the shift in the phase equilibrium of the ammonium to the ammonia gas. The fourth member is configured to act on the ammonia gas. The optoelectronic reader includes a light emitting diode (LED) configured to emit a light towards the sensing cartridge, and a photodiode configured to sense reflected light from the sensing cartridge and to provide a measurement based on the reflected light. The processor is configured to quantify the ammonia gas based on the measurement.

It is understood that other aspects of apparatuses and methods will become readily apparent to those skilled in the art from the following detailed description, where various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein:

FIG. 7 illustrates an application of a feed solution to a member set of a sensing cartridge, where the member set includes four members.

FIG. 8 illustrates an application of a feed solution to a member set of a sensing cartridge, where the member set includes different sized members.

FIG. 12 is a table of permeate wicking properties of a second member of a sensing cartridge.

FIG. 23 is a table of cellular components of bodily fluids and of water.

FIG. 24 is a table of phase change equilibriums for a plurality of species.

DETAILED DESCRIPTION

Figure 1:
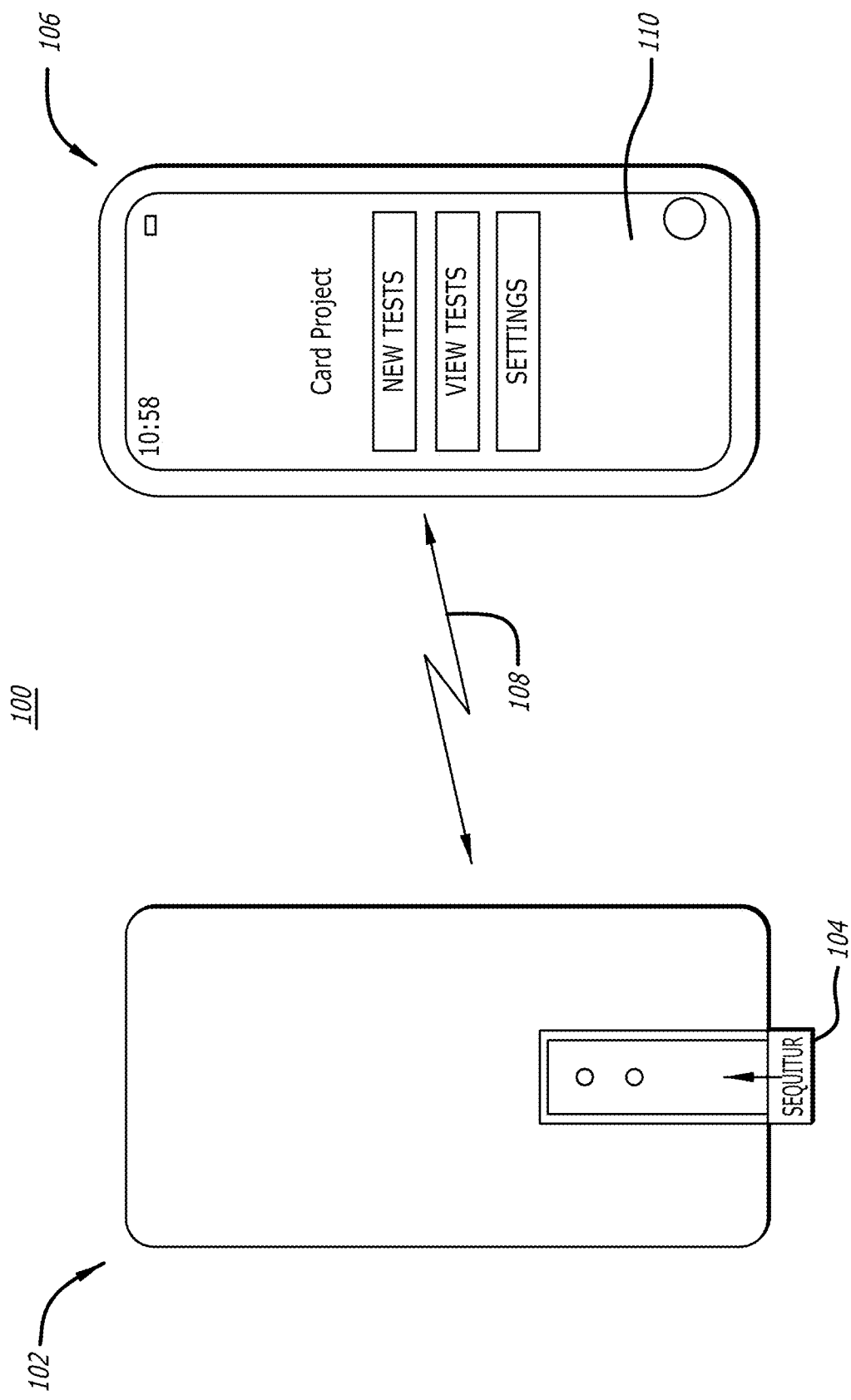
FIG. 1 depicts a system for measuring a permeate from a feed solution including an optoelectronic reader, a sensing cartridge, and a display device.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

In clinical laboratory medicine, ammonia gas ($NH_3$), ammonium ions ($NH_4^+$), total ammonia (e.g., sum of dissolved ammonia gas and ammonium ions), carbon dioxide gas ($CO_2$), bicarbonate ions ($HCO_3^-$), and total carbon dioxide (e.g., sum of dissolved carbon dioxide gas, bicarbonate ions, and carbonate) are routinely measured in bodily fluids such as plasma, serum, and urine using techniques which involve phase change properties, enzymatic techniques, or partial pressure gas analyzers. Clinical laboratory tests for plasma or serum levels of these analytes may require separation of the plasma or the serum from whole blood through centrifugation prior to measurement. After the separation of plasma or serum, these analytes can be measured using enzymatic, photometric, ion-exchange, and/or ion-specific electrode techniques. However, implementation of the conventional techniques may be limited as instruments for measuring these analytes are expensive, large, often require routine maintenance, and are suitable to be utilized (only) by trained personnel working in clinical laboratory settings. Further, measurements produced by the conventional techniques may be inefficient and/or inaccurate due to a variety of previously described issues, including several confounding variables.

Regarding the measurement of ammonium, and/or total ammonia, plasma, and serum measurements may be easily confounded using current laboratory techniques. Pre-analytical variability of duration and temperature conditions during sample handling may confound conventional techniques. For example, both time and temperature conditions of sample handling impact the degree to which in-sample cellular metabolism increases in-sample total ammonia concentration. Pre-analytical variability in blood sample collection procedures may also confound conventional techniques. For example, both tourniquet use and "milking" of tissue (to produce a sufficient extruded sample of blood for measurement) impact the degree to which in-sample hemolysis occurs which variably impacts in-sample total ammonia concentration. Pre-analytical variability in specific aspects of sample handling procedures may also confound conventional techniques. For example, the variable duration of sample tube uncapping impacts the degree to which ammonia gas escapes from the sample's surface and decreases in-sample total ammonia content as a result. Pre-analytical variability in environmental conditions within the clinical laboratory may also confound conventional techniques. Examples which may each, to variable degrees, impact results of sample analyses include ammonia used in cleansers or ammonia generated by a smoker's residual breath.

Regarding the measurement of carbon dioxide gas, bicarbonate ions, and/or total carbon dioxide, plasma and serum measurements may be easily confounded using conventional clinical laboratory techniques. Pre-analytical variability of duration and temperature conditions occurring during sample handling may confound conventional techniques. For example, both time and temperature conditions of sample handling impact the degree to which in-sample cellular metabolism increases in-sample carbon dioxide gas and decreases in-sample bicarbonate ion content. Pre-analytical variability in specific aspects of sample handling procedures also may confound conventional techniques. For example, the variable duration of sample tube uncapping impacts the degree to which carbon dioxide gas escapes from the sample's surface and decreases in-sample total carbon dioxide content. As an example, carbon dioxide gas escape from an uncapped specimen tube decreases in-sample bicarbonate concentration at a rate of 6 millimoles (mmol) per liter (L) per hour (hr) (mmol/L/hr).

Regarding measurement of ammonium and/or total ammonia, urine measurements may also be easily confounded using conventional techniques. As with blood measurements, variability of duration and temperature conditions occurring during sample handling, specific sample handling procedures, and environmental conditions within the laboratory each, to varying degrees, influence either pre-analytical in-sample ammonia concentration and/or analytical results. More specifically, for urine samples, the highly variable and unpredictably present components of urine may further aggravate pre-analytical in-sample changes of analyte concentration. For example, the pH of urine is much more highly variable compared to blood and may normally range from 4.5 to 8.0 depending on physiological conditions and kidney health. Sample pH influences the degree to which the total ammonia contained within the sample is comprised of ammonia gas and ammonium ion species. For example, within a urine sample with a pH of 5.0, total ammonia is nearly completely ammonium ions with negligible dissolved ammonia gas content. Alternatively, at a pH of 8.0, total ammonia includes a non-trivial portion of dissolved ammonia gas. For such urine samples with relatively high pH, the degree to which confounding may occur with variable duration and temperature conditions of sample handling and variable sample container uncapping is increased. Other components which may be variably contained in urine samples (including free amino acids, proteins, cells, and urease splitting organisms) may also alter pre-analytical in-sample total ammonia content. For example, *Proteus mirabilis, Pseudomonas aeruginosa, Klebsiella species, Morganella morganii*, and Corynebacteria produce urease, which hydrolyses urea into ammonia and carbon dioxide. Because of challenges relating to measuring urine ammonium and total ammonia, clinical practitioners have used "urine anion gap" calculations (based on concentrations of urine sodium, potassium, and chloride) to facilitate an inference (non-quantitative) of whether a specific urine sample had relatively high or relatively low ammonium and/or total ammonia content. However, the urine anion gap may be unreliable.

Arterial and venous blood gas analyses using whole blood samples include measurements or calculations of pH, carbon dioxide gas (partial pressure), oxygen (partial pressure), and total carbon dioxide), and are performed using blood gas analyzers which incorporate primarily electrochemical techniques. Blood gas measurements may be easily confounded. For example, both time and temperature conditions of sample handling impact the degree to which in-sample cellular metabolism increases in-sample carbon dioxide gas and decreases in-sample bicarbonate ion concentration.

Consequently, conventional measurement techniques may be costly, difficult to implement, inefficient, and/or inaccurate.

In accordance with an embodiment, a device for deriving a permeate from a feed solution includes a first member configured to separate a component from a feed solution, wherein the component has a hydrodynamic diameter greater than 0.01 micrometers ($\mu$m), and a second member associated with or coupled to the first member, wherein the second member is configured to wick a permeate from the first member. By separating a component from a feed solution and wicking a permeate, a constituent included in the permeate may be easily extracted and/or measured. As such, measurement techniques that use the derived permeate may be more efficient and/or accurate.

As described herein, a "feed solution" may contain dissolved gases, dissolved ions, solids, and/or biological materials. The feed solution may be an aqueous source. Examples of the aqueous source include water, groundwater, surface water, reclaimed water, ocean water, industrial water, industrially produced water, and medical wastewater (e.g., dialysis water production effluent). The feed solution may also be a bodily fluid produced by a living organism. The bodily fluid can be complex and consist of a solvent (e.g., water) with various solutes and/or suspended biological materials (e.g., dissolved gases, ions, compounds, inorganic molecules, organic molecules, amino acids, proteins, cells, etc.). Examples of bodily fluids include, but are not limited to, blood, whole blood, blood plasma, blood serum, capillary fluid (e.g., commonly acquired following a finger prick or heel stick), interstitial fluid, lymphatic fluid, mucus, sputum, phlegm, pus, cerebrospinal fluid, pericardial fluid, pleural fluid, peritoneal fluid, saliva, vomit, gastric fluid, bile, chyle, colonic fluid, urine, sweat, sebum, cerumen, lacrimal fluid (tears), rheum, aqueous humor, vitreous humor, synovial fluid, amniotic fluid, breast milk, semen, transudate fluid, exudate fluid, serous fluid, intracellular fluid, and extracellular fluid.

Whole blood may be a complex solution, often referred to as a living tissue, with a highly variable composition. By volume, whole blood may be approximately 55% plasma and 45% cellular components. Blood may be a body tissue that consists of substances dissolved and suspended in body fluid plasma or serum. Examples of the substances may include amino acids, proteins, platelets, red blood cells, white blood cells, etc. Plasma may be, for example, 90-92% water, and 8-10% proteins. To distinguish "plasma" from "serum," plasma may be defined as the volume of fluid in an unclotted whole blood sample. Plasma contains clotting factors. Overall, the proteins in plasma include fibrinogen and other clotting factors, globulins which participate in the immune response, and albumin which helps maintain osmotic balance. Plasma also contains ions and small molecules such as sodium, chloride, magnesium, calcium, ammonium, potassium, hydrogen, hydroxide, amino acids, glucose, and vitamins. Serum, in contrast to plasma, may be the volume of fluid that remains following clotting of a whole blood sample. Serum may not contain clotting factors. Serum's volume may be slightly less than that of plasma.

As described herein, a "component" may be a microorganism (e.g., bacteria, algae, yeast, fungi, viruses, etc.), a cellular component (e.g., red blood cells), or other component (e.g., an ion, salt, molecule, protein, molecular therapeutic, etc.) included in a feed solution (e.g., whole blood). Examples of components included in whole blood include erythrocytes (red blood cells), leukocytes (white blood cells), and/or thrombocytes (platelets). Other examples of components include hemoglobin, glucose, lipids, albumin, amino acids, creatinine, urea, or a therapeutic molecule.

As described herein, and as commonly used in the field of membrane science, a "permeate" may be a liquid or fluid that is separated from a feed solution by selective transport through a membrane or similar structure. Remaining feed liquid or other components that do not pass through the membrane may be referred to as "retentate." The permeate may be a material or fluid which has passed through a permeable membrane or a semipermeable membrane with macropores (pores with diameters >50 nanometers (nm)), mesopores (pores with diameters 2-50 nm), or micropores (pores with diameters <2 nm), or a dense structure where the permeate is separated from other components in the feed solution. As an example, if the feed solution is whole blood, the permeate may be plasma or serum from whole blood while the retentate contains larger components present in the whole blood (e.g., red blood cells, white blood cells, etc.). As another example, if the feed solution to a macroporous membrane is wastewater containing microorganisms at a concentration of 6.6×10^6 colony forming units of *Escherichia coli* (*E. coli*) per milliliter of feed solution, then the permeate may be water with a concentration of microorganisms less than 1.5×10^3 colony forming units of *E. coli* per milliliter of permeate water. As another example, if the feed solution to a dense semipermeable membrane is saline water containing sodium chloride or other salts at a concentration of 2-30 grams (g) per Liter (L) (g/L), then the permeate may be water with a concentration of sodium chloride or salts <1 g/L. As another example, if the feed solution is a bodily fluid such as urine, then after passing through a microporous or dense semi-permeable membrane, the retentate may be concentrated urine containing large cellular components with average diameters greater than the average pore diameter of the membrane pores, and the permeate will be liquid, primarily water with components with hydrodynamic radii smaller than the average pore diameter of the membrane pores. In addition, the liquid may be a flowable material that includes at least one component that is a true liquid under conditions of treatment (e.g., a slurry, wet sludge, pumpable sediment, emulsion, froth, etc.)

As described herein, a "constituent" may be a dissolved ionic species or a dissolved gas. Examples of the dissolved ionic species include ammonium ($NH_4^+$), bicarbonate ($HCO_3^-$), carbonate ($CO_3^{2-}$), carbon monoxide (CO), cyanuric acid (HCN), chloride ($Cl^-$), proton ($H^+$), nitrate ($NO_3^-$), nitrite ($NO_2^-$), arsenite ($AsO_3^{3-}$), arsenate ($AsO_4^{3-}$), and sulfate ($SO_4^{2-}$). Examples of the dissolved gas include ammonia ($NH_3$), carbon dioxide ($CO_2$), carbon monoxide (CO), cyanuric acid (HCN), chlorine ($Cl_2$), hydrogen ($H_2$), nitrogen dioxide ($NO_2$), nitric oxide (NO), diarsenic trioxide ($As_2O_3$), diarsenic pentaoxide ($As_2O_5$), sulfur dioxide ($SO_2$).

As described herein, "separate" or "separating" may refer to the disassociation of a component from a feed solution. For example, separating may not only imply separating retentate and a permeate from a feed solution, but disassociation of a component from a feed solution. In an embodiment, separating the component from the feed solution involves separating solids from a liquid. In another embodiment, separating the component from the feed solution involves separating a liquid from a liquid by a solid separating medium via an opening in the medium or between discrete particles.

As described herein, "wick" or "wicking" may refer to the drawing off of a liquid (e.g., a feed solution, a permeate, or the like) via capillary action. In an embodiment, the capillary action may be induced by a structure (e.g., a channel or a pore) and/or surface tension. In another embodiment, the capillary action may be induced by a chemical potential gradient to enable quick drawing of a permeate. Capillary action (sometimes referred to as "capillarity" or "capillary forces") may be described as the tendency for a liquid in a capillary tube or absorbent material to rise or fall as a result of surface tension.

FIG. 1 depicts a system 100 for deriving a permeate from a feed solution and quantifying a constituent of the feed solution. The system 100 includes an optoelectronic reader 102, a sensing cartridge 104, and a display device 106.

The optoelectronic reader 102 is configured to receive and removably couple with a sensing cartridge 104. The optoelectronic reader 102 is also configured to obtain measurements of reflected light from the sensing cartridge 104 and to quantify a constituent of the feed solution based on the measurements. A constituent may be quantified, for example, in terms of an amount or concentration. In an embodiment, the optoelectronic reader 102 includes a plurality of components (not shown) that allow the optoelectronic reader 102 to measure and quantify based on reflected light and to provide data to the display device 106. The plurality of components may include a light emitting diode (LED), a sensing photodiode, a microchip with memory and a processor, a communications interface, a printed circuit board (PCB) board, electronic environmental sensors (e.g., for temperature, relative humidity, and/or pressure detection), a power supply (e.g., a battery), status indicating lights, and/or a receptacle for the sensing cartridge 104. By including the plurality of components in the optoelectronic reader 102, the optoelectronic reader 102 is able to operate as a handheld, wireless device, which increases measurement efficiency and user accessibility. An example of the optoelectronic reader 102 is described in further detail with reference to FIGS. 2A and 2B.

In another embodiment, the reader may be an electronic reader. In this embodiment the reader includes one or more the gas-sensing electrodes in place of the LEDs and sensing photodiodes. The electronic reader includes a microchip with memory and a processor, a communications interface, a printed circuit board (PCB) board, electronic environmental sensors (e.g., for temperature, relative humidity, and/or pressure detection), a power supply (e.g., a battery), status indicating lights, and/or a receptacle for the sensing cartridge 104.

In either embodiment, components of the reader may communicate with each other via a data and control bus. The processor may include a microprocessor, a central processing unit, an application specific integrated circuit (ASIC), a field programmable gate array (FPGA), a digital signal processor (DSP) and/or a network processor. The processor may be configured to execute processing logic, e.g., algorithms, software instructions, etc., stored in memory for performing the operations described herein. In general, the processor may include any suitable special-purpose processor specially programmed with processing logic to perform the operations described herein.

Memory may include, for example, without being limited to, at least one of a read-only memory (ROM), a random access memory (RAM), a flash memory, a dynamic RAM (DRAM) and a static RAM (SRAM), storing computer-readable instructions executable by processing device. In general, memory may include any suitable non-transitory computer readable storage medium storing computer-readable instructions executable by the processor for performing the operations described herein. In some examples, the reader may include two or more memory devices (e.g., dynamic memory and static memory).

The sensing cartridge 104 is removably coupled to the optoelectronic reader 102. As an example, "removably coupled" may imply that a component (e.g., a sensing cartridge) may be mounted and/or dismounted to another corresponding component (e.g., an optoelectronic reader) via a coupling mechanism (e.g., a latch, a pin, a spring, a magnet, or other coupling mechanism). By allowing the sensing cartridge 104 to be mounted/dismounted to/from the optoelectronic reader 102, feed solutions may be easily added to the sensing cartridge 104, and the sensing cartridge may be easily replaced or serviced. Examples of the sensing cartridge 104 are described in further detail with reference to FIGS. 3A-3E.

The display device 106 wirelessly connects to the optoelectronic reader 102 via a wireless connection 108. Examples of the wireless connection 108 include Bluetooth, Bluetooth Low Energy (BLE), Wi-Fi, Ultra-Wideband (UWB), or other similar radio communications. In an embodiment, the display device 106 is configured to communicate with the optoelectronic reader 102 via the wireless connection 108. For example, the display device 106 is configured to receive data (e.g., constituent quantifications, raw measurements, measurement change value) provided by the optoelectronic reader 102, to process the data, and to display the data to a user. The display device 106 displays the data to the user via a graphical user interface (GUI) 110. As an example, the GUI 110 is produced by a computer program or software application. Examples of the display device 106 include a smartphone, a smartwatch, a computer, and other similar devices that are capable of displaying the data provided by the optoelectronic reader 102.

Although the system 100 is shown as including a display device 106, in some embodiments, the system 100 may not include the display device 106. In such embodiments, the optoelectronic reader 102 may include a display (not shown) and/or a GUI (not shown) for displaying data to a user. As an example, the display and/or the GUI may be on an outer surface of the optoelectronic reader 102. In such an example, the display and/or the GUI may be controlled by a user to configure display settings, data settings, test settings, etc.

Figure 2A:
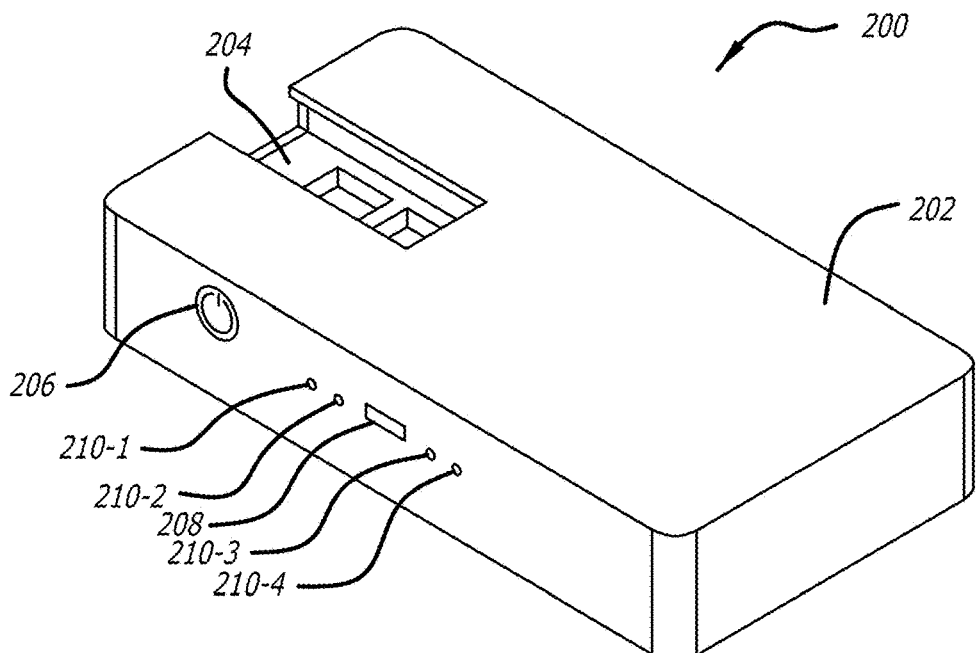
FIG. 2A depicts an isometric view of an optoelectronic reader.

FIG. 2A depicts an isometric view of an optoelectronic reader 200. The optoelectronic reader 200 may represent an embodiment of the optoelectronic reader 102 shown in FIG. 1. The optoelectronic reader 200 includes a housing 202, a sensor port 204, a power button 206, a Universal Serial Bus (USB) Type-C (USB-C) port 208, four LEDs, implemented as LED1 210-1, LED2 210-2, LED3 210-3, and LED4 210-4, and optional environmental ports (not shown).

The housing 202 encloses a plurality of components (not shown) (e.g., a LED, a sensing photodiode, a microchip, a communications interface, a PCB board, electronic environmental sensors (e.g., for temperature, relative humidity, and/or pressure detection), a power supply, status indicating lights, and/or a receptacle for the sensor. The housing 202 may be a three-dimensional (3D) prismatic shape with a plurality of outer surfaces. The plurality of the outer surfaces may be curved, flat, angled, or any combination thereof. Additionally, the housing 202 includes a plurality of openings for the sensor port 204, the power button 206, the USB-C port 208, the LEDs 210-1, 210-2, 210-3, and 210-4, and the environmental ports. The openings may be circular, rectangular, trapezoidal, etc., and may be on one or more of the outer surfaces of the housing 202. For example, openings for the power button 206, the USB-C port 208, and the LEDs 210-1, 210-2, 210-3, and 210-4 are on a first outer surface, openings for the environmental ports are on a second outer surface, and an opening for the sensor port 204 is on a third outer surface.

The sensor port 204 is configured to hold a sensing cartridge (e.g., sensing cartridge 104). For example, the sensing cartridge can be inserted in the sensor port 204, mounted to the sensor port 204, and/or removably coupled to the sensor port 204. In an embodiment, the sensor port 204 is a rectangular opening that is parallel to a LED and to a sensing photodiode (described in further detail with reference to FIG. 2B) inside the housing 202. As such, when the sensor port 204 is holding the sensing cartridge, the sensing cartridge may be parallel to and/or approximately across from the LED and the sensing photodiode. The sensor port 204 may also include a transparent layer (e.g., glass, plexiglass, or other similar transparent material) to allow light to be emitted by the LED onto the sensing cartridge, reflected by the sensing cartridge, and then measured by the sensing photodiode. Although the sensor port 204 is shown as being in the middle of an outer edge of the optoelectronic reader 200, the sensor port may also be on another edge and/or other outer surface of the optoelectronic reader.

The power button 206 is configured to power on/off the optoelectronic reader 200 and/or to reset the optoelectronic reader 200. As shown, the power button 206 is positioned near a corner of the optoelectronic reader 200, but may also be positioned elsewhere on the optoelectronic reader 200. Additionally, although not shown, the power button 206 may be a switch or other power control mechanism for powering on/off the optoelectronic reader 200.

The USB-C port 208 is connected to a power supply of the optoelectronic reader 200 and is configured to house a USB-C input. In an embodiment, the optoelectronic reader 200 charges when the USB-C input is connected to the USB-C port 208. As shown, the USB-C port 208 is positioned between LED2 210-2 and LED3 210-3, but may also be positioned elsewhere on the optoelectronic reader 200. Additionally, although the USB-C port 208 is configured to house a USB-C input, the USB-C port may also be a micro USB port, a USB Type-A port, a mini USB port, an 8-Pin Lightning port, or other charging port that houses a corresponding input.

The LEDs 210-1, 210-2, 210-3, and 210-4 emit colored lights that correspond to predefined indications. For example, LED1 210-1 emits a yellow/orange light which indicates "low battery," LED2 210-2 emits a red light which indicates "battery charging," LED3 210-3 emits a white light which indicates "power on," and LED4 210-4 emits a blue light which indicates "Bluetooth connected."

Although the LEDs 210-1, 210-2, 210-3, and 210-4 are described as emitting certain colored lights with predefined indications, the LEDs are not limited to such colors and/or indications. For example, the LEDs may change colors and/or blink to indicate that the optoelectronic reader 200 is in a Bluetooth pairing mode, a measuring mode, a reset mode, etc. Additionally, although the optoelectronic reader 200 is shown as including four LEDs, the optoelectronic reader 200 may include less than four LEDs or more than four LEDs.

Although not shown, the optoelectronic reader 200 may also include environmental ports that are configured to connect to peripheral devices such as, for example, monitors, computers, mobile devices, and the like. In an embodiment, the environmental ports are configured to provide data (e.g., measurements) to the peripheral devices. In an embodiment, there are four environmental ports arranged adjacent to one another in a spatial grouping. Although the optoelectronic reader 200 may include four environmental ports in a certain spatial arrangement, the optoelectronic reader may also include less than or more than four environmental ports in a different spatial arrangement.

As an example, the optoelectronic reader 200 may have a length greater than 11.3 centimeters (cm), a width greater than 5.5 cm, and a height greater than 2.6 cm. Additionally, although the optoelectronic reader 200 is described as having certain dimensions and a plurality of components, the optoelectronic reader 200 is not limited to such dimensions and/or components.

Figure 2B:
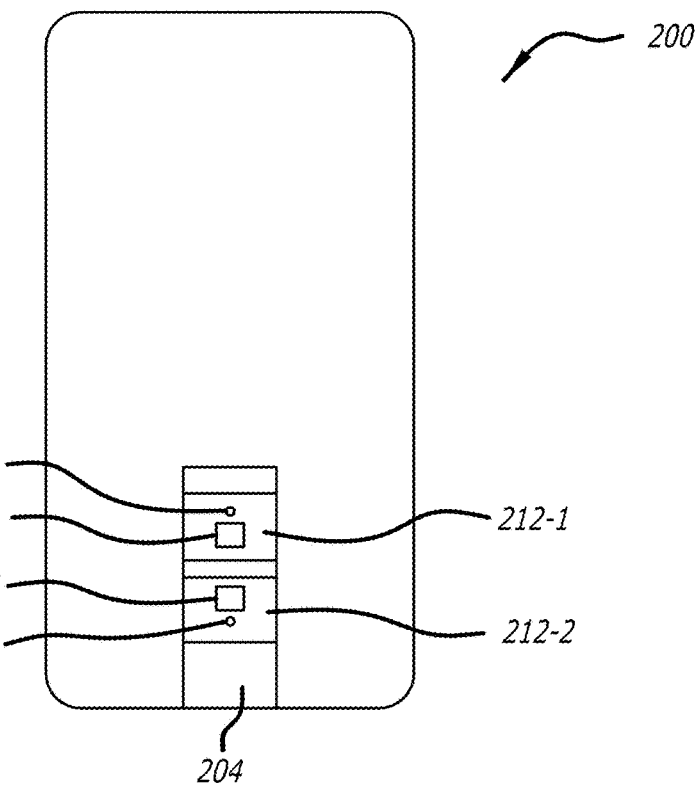
FIG. 2B depicts a top perspective view of the optoelectronic reader of FIG. 2A.

FIG. 2B depicts a top perspective view of the optoelectronic reader 200 of FIG. 2A. As shown, the top perspective view of the optoelectronic reader 200 depicts the sensor port 204 as described with reference to FIG. 2A. The optoelectronic reader 200 is also shown as including two quantifying components, implemented as a first quantifying component 212-1 and a second quantifying component 212-2.

The first quantifying component 212-1 is aligned adjacently to the second quantifying component 212-2, such that the first quantifying component 212-1 and the second quantifying component 212-2 may be symmetric. As an example, an edge of the first quantifying component 212-1 is separated from an edge of the second quantifying component by at least 10 millimeters (mm). In an embodiment, the quantifying components 212-1 and 212-2 are positioned near the center of the sensor port 204.

The quantifying components 212-1 and 212-2 may use an absorbance-based technique to quantify a frequency response. In an embodiment, the quantifying components 212-1 and 212-2 include amperometric detectors, voltammetric detectors, and/or potentiometric detectors. The quantifying components 212-1 and 212-2 may produce data that comes from quantitative measurements, semi-quantitative measurements, or qualitative measurements. In an exemplary embodiment, the quantifying components 212-1 and 212-2 use a reflectance or reflectance-absorbance hybrid detection system to produce the data. Examples of the data include ammonia level readings for gas extracted from a feed solution or ammonia levels extracted from a liquid bodily fluid. In some embodiments, measurements of ammonia values or levels may be periodically collected over time, e.g., once an hour, once a day, etc., to obtain a series of measurements for comparison to a baseline ammonia level. In some embodiments, the measurements are obtained using different sensing cartridges. The comparison outcome, e.g., are the obtained measurements trending toward or away from the baseline, provide useful feedback that may be indicative of a patient's evolving liver health status and effectiveness of ammonia-lowering mediations. In wastewater treatment plants, ammonium in water may be measured serially (e.g., one or more times daily) and compared to previous values to evaluate the effectiveness of treatment techniques in reducing the ammonium.

The quantifying components 212-1 and 212-2 may each include a LED and a sensing photodiode. As shown, the first quantifying component 212-1 includes a first LED 214-1 and a first sensing photodiode 216-1, and the second quantifying component 212-2 includes a second LED 214-2 and a second sensing photodiode 216-2. The LEDs 214-1 and 214-2 are configured to emit a light towards a sensing cartridge (e.g., sensing cartridge 104). In an exemplary embodiment, the LEDs 214-1 and 214-2 are thin film chip technology configured to emit a light with a wavelength of 606 nanometers (nm) and a radiation type 120° (Lambertian emitter) with corrosion robustness class 3B. As an example, the LEDs 214-1 and 214-2 may be "OSRAM LO M67F" LEDs. The sensing photodiodes 216-1 and 216-2 are configured to detect/sense reflected light (produced by the LEDs 214-1 and 214-2) from the sensing cartridge, and to provide a measurement, e.g., a voltage, based on the reflected light. In an exemplary embodiment, the sensing photodiodes 216-1 and 216-2 have dimensions of 6.4 mm×3.9 mm×1.2 mm with an angle of half sensitivity of ±65°, a floor life of 168 hours, moisture sensitivity level (MSL) 3, lead-free reflow soldering, and are halogen-free. As an example, the sensing photodiodes 216-1 and 216-2 may be "Vishay Semiconductors VBPW34S, VBPW34SR" photodiodes.

Although the optoelectronic reader 200 is shown as including two quantifying components 212-1 and 212-2, two LEDs 214-1 and 214-2, and two sensing photodiodes 216-1 and 216-2, the optoelectronic reader may also include less than or more than two quantifying components, LEDs, and/or sensing photodiodes. Additionally, the quantifying components 212-1 and 212-2 are not limited to such positioning or features as described with reference to FIG. 2B.

Figure 3A:
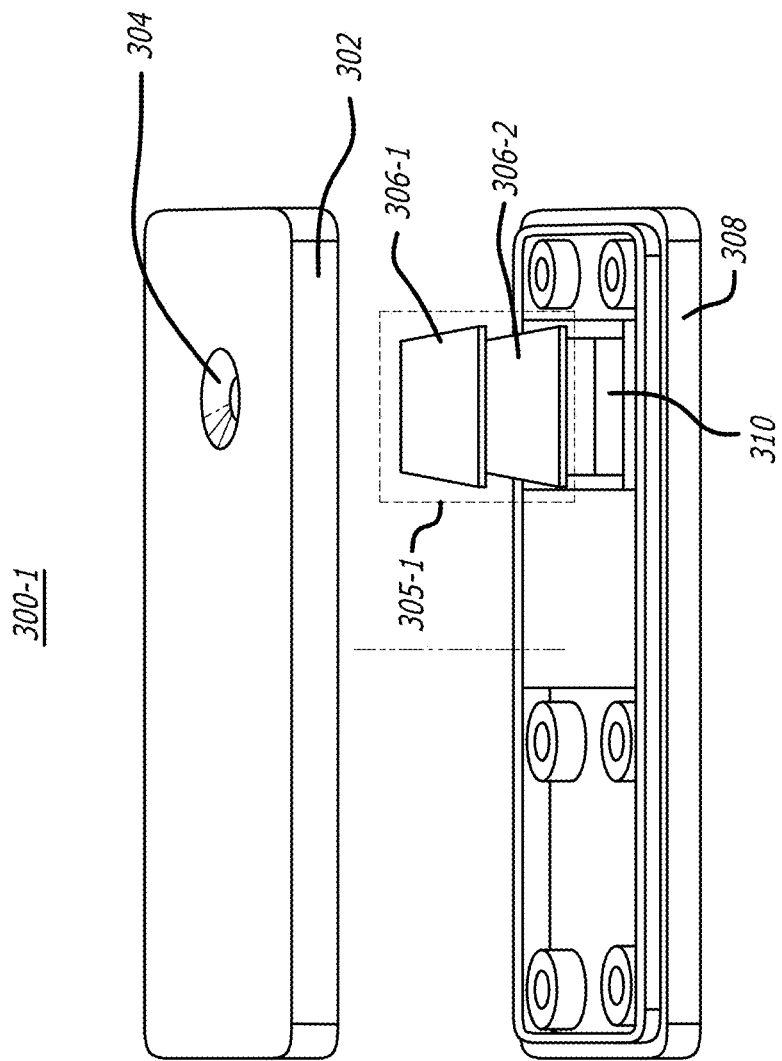
FIG. 3A depicts a sensing cartridge with a member set having two members.

FIG. 3A depicts a sensing cartridge 300-1 with a member set having two members. The sensing cartridge 300-1 may represent an embodiment of the sensing cartridge 104 shown in FIG. 1. As shown, the sensing cartridge includes a top casing 302 with a feed input 304, a first member set 305-1 which includes a first member 306-1 and a second member 306-2, and a bottom casing 308 with a window 310. In some embodiments, the first member 306-1 and the second member 306-2 may be combined as a composite member. Although FIG. 3A shows the components of the sensing cartridge 300-1 as being separated, the components may be coupled together such that the top casing 302 connects to the bottom casing 308 (e.g., via pins) and contains the first member 306-1 and the second member 306-2.

The top casing 302 with the feed input 304 is configured to receive a feed solution, such that the feed solution may be placed in the feed input 304. The feed input 304 of top casing 302 allows the feed solution to come in contact with the first member 306-1 (e.g., via a hole or an opening). The feed input 304 may be circular, rectangular, etc. As an example, the feed input 304 is positioned along a center axis of the top casing 302.

The first member 306-1 is configured to separate a component from the feed solution. As an example, the component has a hydrodynamic diameter greater than 0.01 micrometers (μm). In some embodiments, the first member includes a microfluidic structure with channel diameters of less than 2,000 μm for separating the component from the feed solution. In some embodiments, the first member includes a separating layer that separates the component from the feed solution. The separating layer may be a membrane filter with an average pore size greater than 0.01 μm and a void volume between 0.5 microliters (μL) per square centimeter ($cm^2$) ($\mu L/cm^2$) and 60 $\mu L/cm^2$. Examples of the membrane filter include an organic membrane, an inorganic membrane, a mixed matrix membrane, a composite membrane, a symmetric membrane, and an asymmetric membrane. As an example, the asymmetric membrane is typically made from a polymeric material and has a gradient in pore size and material density throughout a cross section of the membrane, such that one surface has smaller and more dense pores than the other surface. Examples of the membrane for the first member 306-1 are described in further detail with reference to FIG. 10.

The second member 306-2 is configured to wick a permeate from the first member 306-1. In one embodiment, the second member 306-2 is configured to act on a constituent in the permeate to shift a phase equilibrium of the constituent to a gaseous state. In another embodiment, the second member 306-2 is configured to transport the permeate to another member that is configured to act on the constituent in the permeate to shift the phase equilibrium of the constituent to the gaseous state.

In one embodiment, the second member 306-2 includes a process, an additive, or a catalyst to act on the constituent in the permeate to shift the phase equilibrium of the constituent to the gaseous state. In another embodiment, the second member 306-2 includes an additive that induces the shift in the phase equilibrium of the permeate by changing a pH of the permeate to form an alkaline fluid with a pH of at least 8. Examples of an alkaline pH changing additive or combination of additives include sodium hydroxide, sodium carbonate, sodium bicarbonate, sodium tetraborate, or sodium hydrogen orthophosphate. In yet another embodiment, the second member 306-2 includes an additive that induces the shift in the phase equilibrium of the permeate by changing a pH of the permeate to form an acidic fluid with a pH of at most 6.5. Examples of an acidic pH changing additive or combination of additives include low-vapor pressure acids (e.g., citric acid, ascorbic acid, and lactic acid).

As described herein, an "additive" is an agent that is added to a liquid (e.g., permeate) being treated to either cause a desired result or to promote a result which would not occur, occur more slowly, or occur incompletely without the additive. Examples of an additive include filter aids, chemical agents, seeding agents, and buffers.

In some embodiments, the second member 306-2 induces the shift in the phase equilibrium of the permeate by changing a temperature of the permeate to affect solubility of a gas in the permeate. As an example, the temperature of the permeate is changed via nanophotonic materials included in the second member 306-2, such that the nanophotonic materials heat when irradiated with light in a visible spectrum. As another example, the temperature of the permeate is changed via a conductive member included in the second member 306-2. To this end, the sensing cartridge 300-1 can include an electrical interface through which an electrical current is applied to the conductive member to resistively heat the second member 306-2. The electrical interface of the sensing cartridge 300-1 is configured to couple with an electrical interface of the optoelectronic reader 102, where the reader is the source of the electrical current.

The second member 306-2 may also include a wicking layer that wicks the permeate from the first member 306-1. Examples of the wicking layer include a woven paper, a non-woven paper, a membrane, a structure of natural fiber, a structure of synthetic fiber, a porous material, and a material. Examples of the material include cotton materials and cotton derivatives, cellulose materials and cellulose derivatives, ethylcellulose materials and ethylcellulose derivatives, nitrocellulose materials and nitrocellulose derivatives, polyester materials and polyester derivatives, nylon materials and nylon derivatives, glass-fiber materials and glass-fiber derivatives, silica, titanium dioxide, carbon-based materials and carbon-based derivatives, organic nanoparticles, inorganic nanoparticles, and polyester terephthalate materials and polyester terephthalate derivatives that further include a pore structure that enables capillary forces to draw the permeate into a void structure of the second member and a void volume that enables gas diffusion.

The second member 306-2 may also include hydrophobic patterned areas that penetrate through the second member 306-2. The hydrophobic patterned areas may be on a portion or on all of the second member 306-2. In an embodiment, the hydrophobic patterned areas exhibit hydrophobic deionized water droplet contact angles. The hydrophobic deionized water droplet angles may include hydrophobic materials such as, for example, bees wax, paraffin, polydimethyl siloxane, polytetrafluoroethylene, polyvinylidene fluoride, cellulose, carbon-based materials, nanoparticles, silicon-based materials, or printing inks. The hydrophobic material may be implemented on the second member 306-2 via screen printing, wax printing, solution casting, or spraying. Examples and features of the second member are described in further detail with reference to FIGS. 11-13.

The first member 306-1 and/or the second member 306-2 may each have a length greater than 2 mm, a width greater than 2 mm, and a height greater than 10 micrometers ($\mu m$). The first member 306-1 and the second member 306-2 may include impregnation with one or more chelating agents (e.g., $Cu^{2+}$) to bind to and to trap amino acids in the feed solution or the permeate. The first member 306-1 and the second member 306-2 may be in complete contact or partial contact with each other. The first member 306-1 and the second member 306-2 are associated with each other or coupled to allow interfacial contact that enables flow of liquids and gases limiting resistance and backpressure. For example, the contact may be sufficient interfacial contact that enables a formation of pathways that allow the flow of liquids and gases with minimization of resistance to flow and backpressure. The flow of the liquids and the gases may be vertical, lateral, or a combination thereof. Although the first member 306-1 and the second member 306-2 are shown as being rectangular, the first member 306-1 and the second member 306-2 may also be circular or another similar shape.

The bottom casing 308 with the window 310 is configured to allow gas to diffuse from the second member 306-2 (e.g., via a hole or an opening). In an embodiment, the window 310 is a diffusion window. The window 310 may be circular, rectangular, etc. As an example, the window 310 is positioned along a center axis of the bottom casing 308. The window 310 may align with a quantifying component (e.g., a first quantifying component 212-1 a second quantifying component 212-2) of an optoelectronic reader (e.g., optoelectronic reader 102).

The feed input 304 of the top casing 302, the first member 306-1, the second member 306-2, and the window 310 of the bottom casing 308 may each be centered upon each other. As an example, the sensing cartridge 300-1 may have a length greater than 2 cm, a width greater than 2 mm, and a height greater than 2 mm. The sensing cartridge 300-1 may be made of, for example, a plastic, a metal, a paper, a composite material, or any combination thereof. Although the sensing cartridge 300-1 is described as having certain dimensions and a plurality of members, the sensing cartridge 300-1 is not limited to such dimensions and/or members. For example, although the sensing cartridge 300-1 is shown as being a rectangular shape, the sensing cartridge may also resemble a square, circle, or other similar shape.

In an exemplary embodiment, the sensing cartridge 300-1 is configured to separate plasma from whole blood and shift a phase equilibrium of ammonium to ammonia gas. In the exemplary embodiment, the first member 306-1 is an asymmetric, polysulfone membrane. A first surface of the first member 306-1 accepting the whole blood has a pore size of 100 µm (±25 µm). A second surface of the first member 306-1 contacting the second member 306-2 has a pore size from approximately 500 nm to 1 µm. In the exemplary embodiment, the second member 306-2 is a cellulosic porous filter paper with a thickness of 210 µm and a pore size of 8 µm. To prepare the second member 306-2, the cellulosic porous filter paper is washed in deionized water three times, dip coated in an aqueous alkaline solution with a pH of 12 (e.g., sodium hydroxide), and dried at 60 degrees Celsius (° C.). Planar surfaces of the first member 306-1 and the second member 306-2 are coupled together with the second surface of the first member 306-1 contacting the second member 306-2. In one embodiment, to couple the first member 306-1 and the second member 306-2, edges of the members are melted together using a heat sealer at a temperature above room temperature (e.g., 80° C.) for ten seconds. In another embodiment, to couple the first member 306-1 and the second member 306-2, the members are placed together in the sensing cartridge 300-1.

Figure 3C:
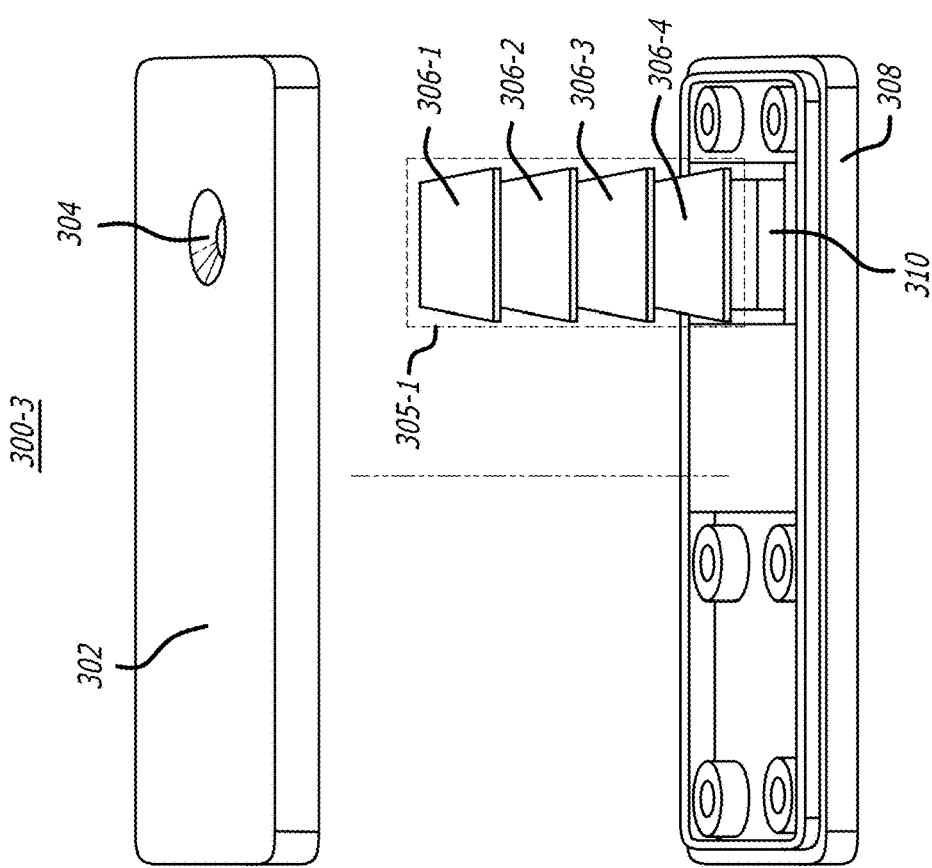
FIG. 3C depicts a sensing cartridge with a member set having four members.
Figure 3B:
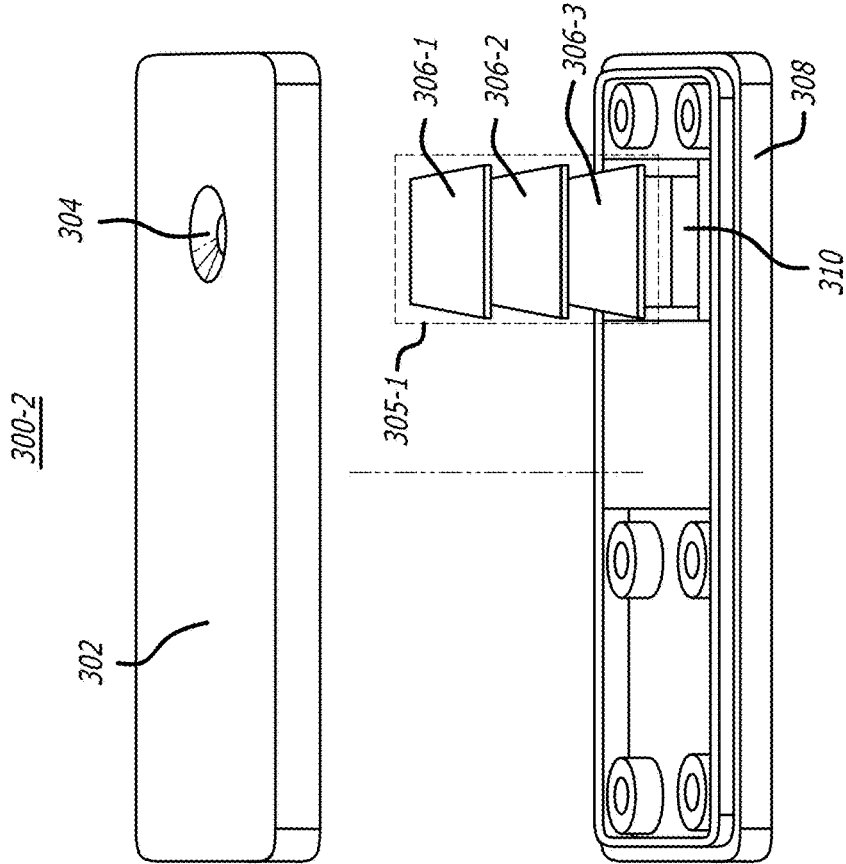
FIG. 3B depicts a sensing cartridge with a member set having three members.

FIG. 3B depicts a sensing cartridge 300-2 with a member set having three members. The sensing cartridge 300-2 may represent an embodiment of the sensing cartridge 104 shown in FIG. 1. The sensing cartridge 300-2 includes the top casing 302, the feed input 304, the first member set 305-1, the first member 306-1, the second member 306-2, the bottom casing 308, and the window 310 as described with reference to FIG. 3A.

In contrast to FIG. 3A, the sensing cartridge 300-2 of FIG. 3B includes a third member 306-3 that is associated with or coupled to the second member 306-2. The third member 306-3 is included in the first member set 305-1 with the first member 306-1 and the second member 306-2. The third member 306-3 is configured to prevent liquid permeation produced by a shift in a phase equilibrium of a constituent to a gaseous state. The third member 306-3 is associated with or coupled to the second member 306-2, such that the third member 306-3 prevents further permeation of liquid permeate from the second member. In some embodiments, the third member 306-3 and the second member 306-2 may be integrated as a composite layer. In an embodiment, the third member 306-3 is a hydrophobic, porous material that prevents liquid from proceeding through the third member and that allows gas diffusion through the third member. As an example, the third member 306-3 is a hydrophobic polymeric membrane with a porosity of greater than 10%, a thickness of less than 200 µm, and/or an average pore size of less than 2 µm. The third member 306-3 may include a supported or unsupported hydrophobic polymeric membrane such as fluoro-polymers. Example properties of the third member are described in further detail with reference to FIG. 14.

In an exemplary embodiment of the sensing cartridge 300-2, the first member 306-1 is an asymmetric, polysulfone membrane, the second member 306-2 is a cellulosic porous filter paper with a thickness of 210 µm and a pore size of 8 µm, and the third member is a porous hydrophobic polytetrafluorethylene membrane with an average pore size of 0.45 µm and a thickness of 50 µm.

FIG. 3C depicts a sensing cartridge 300-3 with a member set having four members. The sensing cartridge 300-3 may represent an embodiment of the sensing cartridge 104 shown in FIG. 1. The sensing cartridge 300-3 includes the top casing 302, the feed input 304, the first member set 305-1, the first member 306-1, the second member 306-2, the third member 306-3, the bottom casing 308, and the window 310 as described with reference to FIG. 3B.

In contrast to FIG. 3B, the sensing cartridge 300-3 of FIG. 3C includes a fourth member 306-4 that is associated with or coupled to the third member 306-3. The fourth member 306-4 is included in the first member set 305-1 with the first member 306-1, the second member 306-2, and the third member 306-3. In some embodiments, the first member 306-1, the second member 306-2, the third member 306-3, and the fourth member 306-4 may be integrated as one composite member. In some embodiments, the third member 306-3 may be a hollow non-wetting spacer (e.g., a plastic ring) that separates the second member 306-2 and the fourth member 306-4, but allows gas to reach the fourth member 306-4.

In an embodiment, the fourth member 306-4 is configured to respond to a diffused gas of a constituent in a permeate. As described herein, "respond to" may imply that the fourth member 306-4 changes a property (e.g., color) proportionally to the quantity of diffused gas present. In another embodiment, the fourth member 306-4 is configured to capture the diffused gas of the constituent in the permeate. As described herein, "capture" may imply that the fourth member 306-4 interacts with the diffused gas such that the gas can be quantified. The fourth member 306-4 may include a gas responsive layer that has a proportional change in response to a quantity of gas present. As an example, the proportional change may be a proportional change in absorbance, a proportional change in absorbance change, or a proportional change in frequency. The gas responsive layer may include a plasmonic nanoparticle or a redox mediator.

In one embodiment, the gas responsive layer includes a polymer coating with a thickness of 1 nm to 100 µm on a transparent substrate (e.g., a polymer or glass), including an indicator, a reactant, and/or a molecule that is responsive to and/or reactive with a gas. In another embodiment, the gas responsive layer includes a pH indicator (e.g., bromophenol blue, bromocresol green, or indophenol) and an alkali, a hydroxide, or a base (e.g., sodium hydroxide, potassium carbonate, sodium carbonate). In such an embodiment, the pH indicator to the alkali or the base is at least 0.5, and the pH indicator or sensing probe is deposited on a transparent substrate with a concentration between 0.001 microgram (µg) per $cm^2$ ($µg/cm^2$) and 100 $µg/cm^2$.

In one embodiment, the first member 306-1, the second member 306-2, the third member 306-3, and the fourth member 306-4 have identical dimensions. In another embodiment, the second member 306-2, the third member 306-3, and/or the fourth member 306-4 have dimensions that are between 50% and 150% of dimensions of the first member 306-1. In an embodiment, "dimensions" may refer to a height, a width, a length, a perimeter, and/or an area of the first member, the second member, the third member, and/or the fourth member. The first member 306-1, the second member 306-2, the third member 306-3, and/or the fourth member 306-4 are associated with or coupled to allow interfacial contact that enables flow of liquids and gases limiting resistance and backpressure. For example, the contact may be sufficient interfacial contact that enables a formation of pathways that allow the flow of liquids and gases with minimization of resistance to flow and backpressure.

Figure 3E:
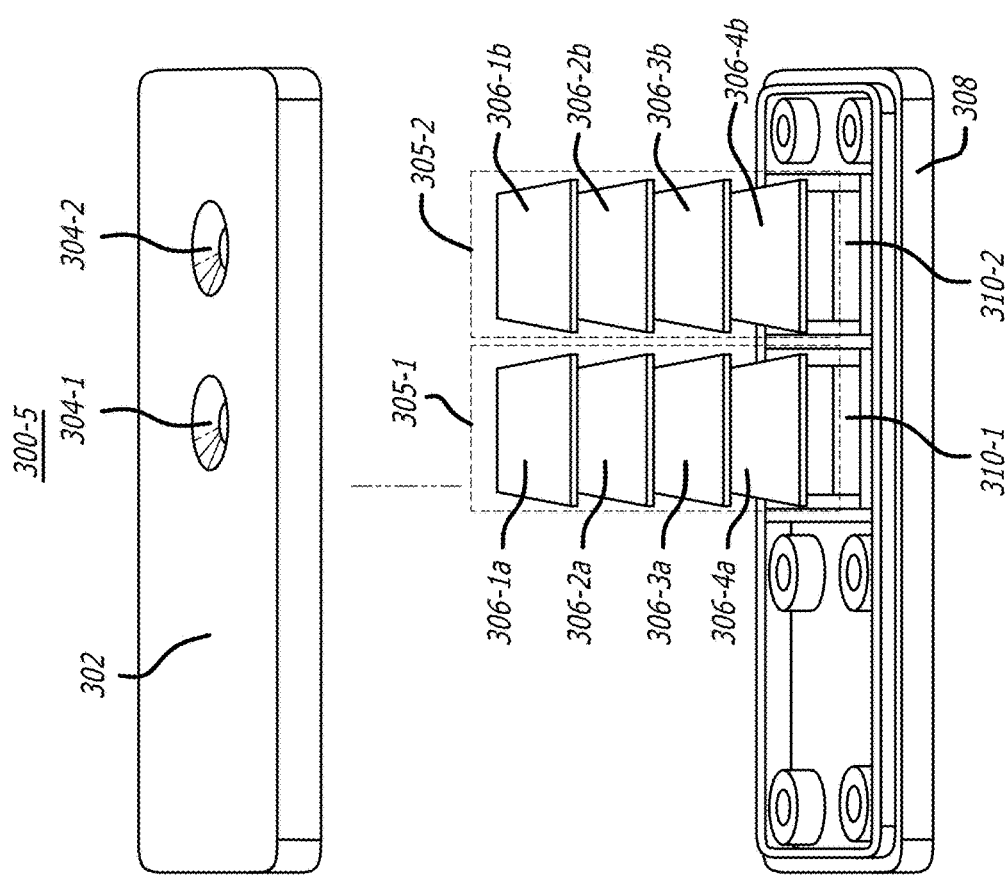
FIG. 3E depicts a sensing cartridge with two member sets having four members.
Figure 3D:
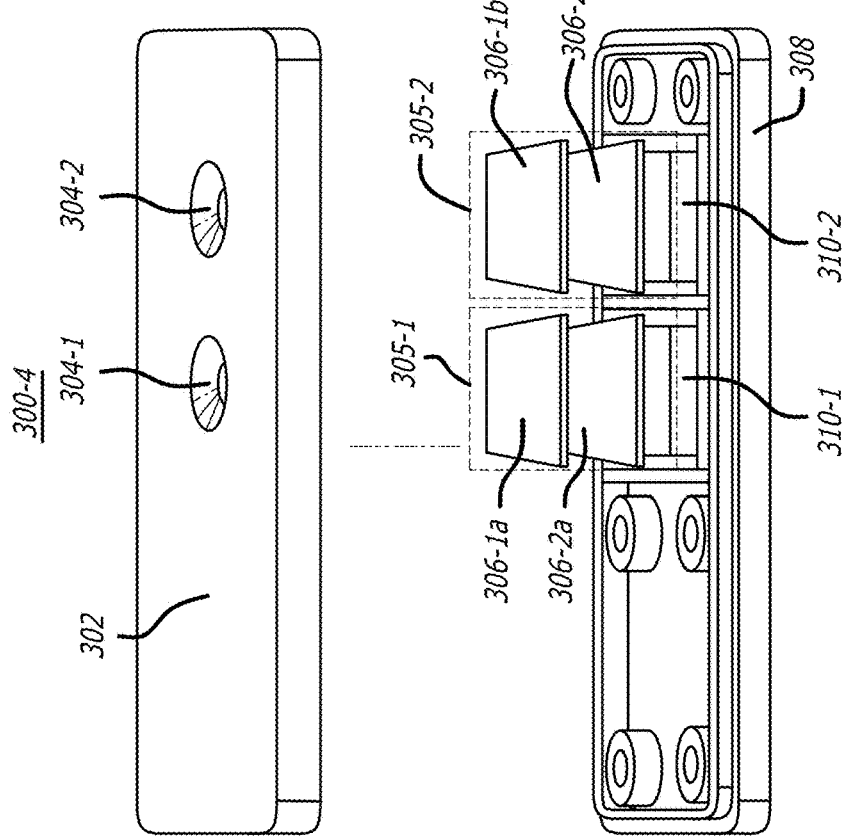
FIG. 3D depicts a sensing cartridge with two member sets having two members.

FIG. 3D depicts a sensing cartridge 300-4 with two member sets, each having two members. The sensing cartridge 300-4 may represent an embodiment of the sensing cartridge 104 shown in FIG. 1. The sensing cartridge 300-4 includes the top casing 302 and the bottom casing 308 as described with reference to FIG. 3A.

In contrast to FIG. 3A, the sensing cartridge 300-4 of FIG. 3D includes two sets of feed inputs, implemented as a first feed input 304-1 and a second feed input 304-2, two sets of first members and second members, implemented as a first member set 305-1 and a second member set 305-2, and two sets of windows, implemented as a first window 310-1 and a second window 310-2. The first member set 305-1 includes a first member 306-1a and a second member 306-2a. The second member set 305-2 includes another first member 306-1b and another second member 306-2b. The feed inputs 304-1 and 304-2, the first members 306-1a and 306-1b, the second members 306-2a and 306-2b, and the windows 310-1 and 310-2 may be as described with reference to FIG. 3A. The windows 310-1 and 310-2 may be diffusion windows. Additionally, the first window 310-1 may align with a first quantifying component 212-1 (FIG. 2B) and the second window 310-2 may align with a second quantifying component 212-2 (FIG. 2B).

FIG. 3E depicts a sensing cartridge 300-5 with two member sets, each having four members. The sensing cartridge 300-5 may represent an embodiment of the sensing cartridge 104 shown in FIG. 1. The sensing cartridge 300-5 includes the top casing 302, the first feed input 304-1, the second feed input 304-2, the first member set 305-1, the first member 306-1a, the second member 306-2a, the second member set 305-2, the other first member 306-1b, the other second member 306-2b, the bottom casing 308, the first window 310-1, and the second window 310-2 as described with reference to FIG. 3D.

In contrast to FIG. 3D, the first member set 305-1 includes a third member 306-3a and a fourth member 306-4a, and the second member set 305-2 includes another third member 306-3b and another fourth member 306-4b. The third members 306-3a and 306-3b and the fourth members 306-4a and 306-4b may be as described with reference to FIG. 3C.

In an embodiment, the first member set 305-1 is used for a control to obtain a reference measurement, and the second member set 305-2 is used for a feed solution to obtain an experimental measurement. To this end, the inlet 304-1 associated with the first member set 305-1 receives a zeroing material from which a first sensing photodiode of the optoelectronic reader obtains baseline measurements, while the inlet 304-2 associated with the second member set 305-2 receives the feed solution from which a second sensing photodiode of the optoelectronic reader obtains constituent measurements. The baseline measurements may be used to correct drift of the second sensing photodiode.

In an exemplary embodiment of the sensing cartridge 300-5, the first members 306-1a and 306-1b are liquid separation members, the second members 306-2a and 306-2b are phase conversion members, the third members 306-3a and 306-3b are gas diffusion members, and the fourth members 306-4a and 306-4b are gas response members. The first members 306-1a and 306-1b are asymmetric, polysulfone membranes, the second members 306-2a and 306-2b are cellulosic porous filter papers with a thickness of 210 µm and a pore size of 8 µm, the third members 306-3a and 306-3b are porous hydrophobic polytetrafluorethylene membranes with an average pore size of 0.45 µm and a thickness of 50 µm, and the fourth members 306-4a and 306-4b are, respectively, a green layer and an ammonia gas responsive layer deposited on a 180 µm thick, transparent polyester terephthalate sheet. The transparent polyester terephthalate sheet has an automated draw-down casting of a solution of 0.1% to 5% bromophenol blue and ethyl cellulose coating, such that the bromophenol blue and ethyl cellulose coating is in contact with the third members 306-3a and 306-3b.

Figure 4A:
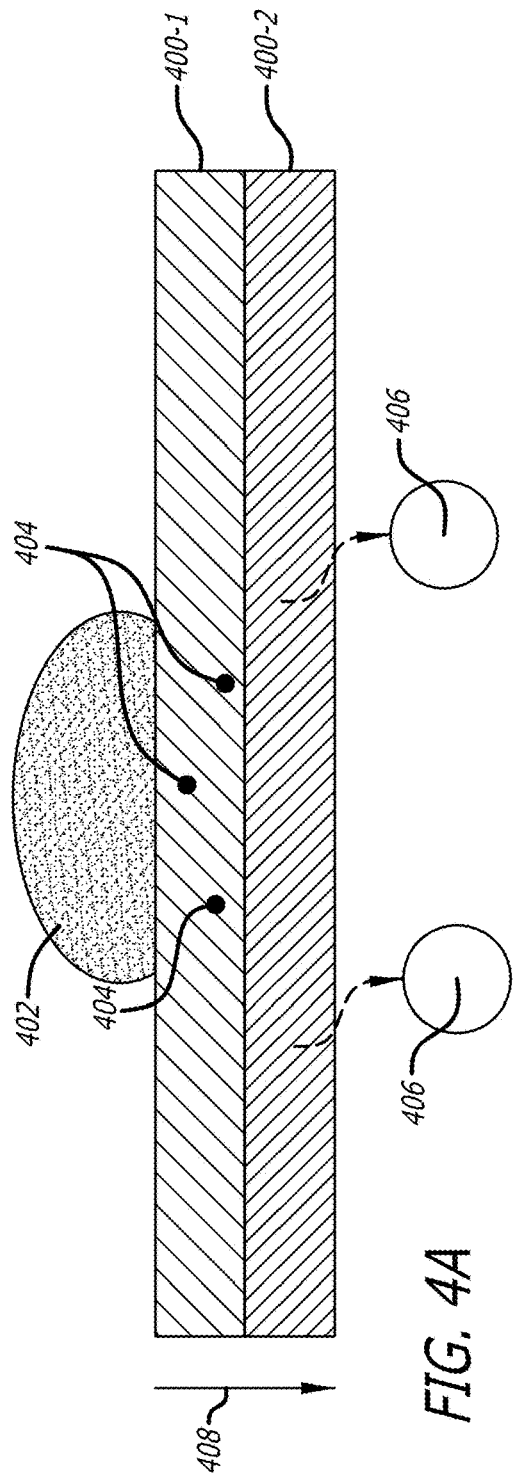
FIG. 4A illustrates an application of a feed solution to a member set of a sensing cartridge, where the member set includes two members.

FIG. 4A illustrates an application of a feed solution to a member set of a sensing cartridge, where the member set includes two members. The member set, which may represent the member set 305-1 of the sensing cartridge 300-1 of FIG. 3A, includes a first member 400-1 and a second member 400-2. The first member 400-1 and the second member 400-2 may respectively correspond to the first member 306-1 and the second member 306-2 described above with reference to FIG. 3A.

In operation, a feed solution 402 is applied to and placed in fluid communication with the first member 400-1. The first member 400-1 is configured to separate components 404 from the feed solution 402, and to retain the components 404 from the feed solution 402. The second member 400-2 is configured to wick a permeate from the first member 400-1, and to act on a constituent in the permeate to shift a phase equilibrium of the constituent to a gaseous state. The induced phase change by the second member 400-2 produces a gas 406 that is extracted from the permeate. As an example, the gas 406 is produced in less than twenty minutes from introduction of the feed solution 402 to the first member 400-1. Arrow 408 represents a direction of flow of the feed solution 402 and permeate through the first member 400-1 and the second member 400-2. The feed solution 402 and the permeate flow primarily vertically through the first member 400-1 and the second member 400-2. "Primarily vertically" as used herein means that between 70-100% of the permeate flows vertically, while the remainder flows laterally.

Figure 4B:
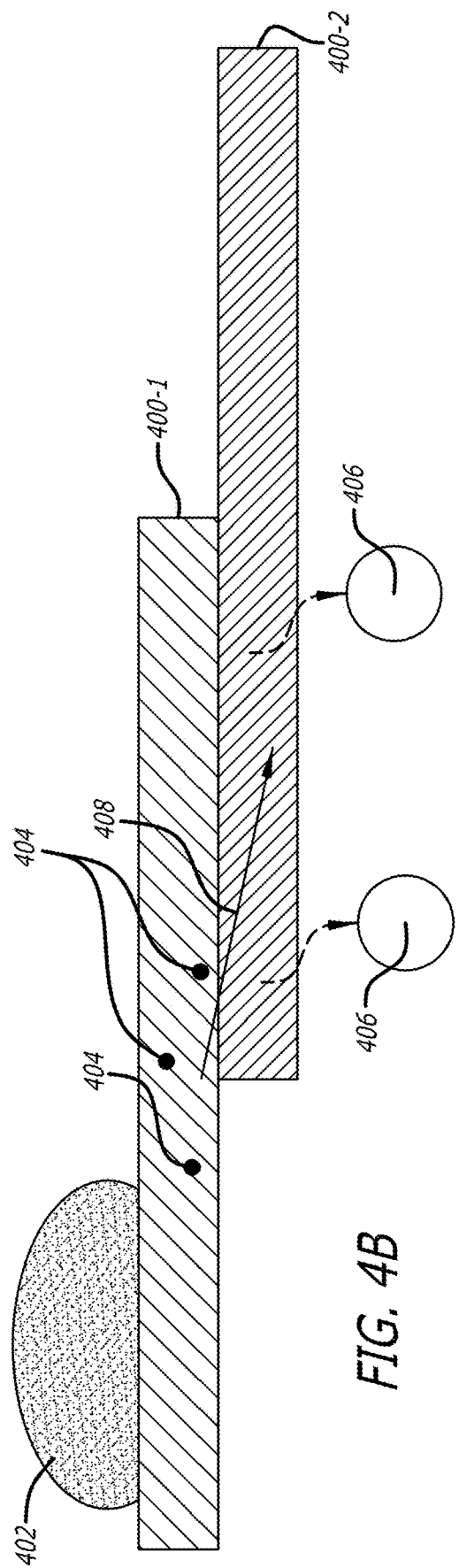
FIG. 4B illustrates another application of a feed solution to a member set of a sensing cartridge, where the member set includes two members.

FIG. 4B illustrates another application of a feed solution to a member set of a sensing cartridge, where the member set includes two members. The member set may represent an alternate embodiment of the member set of FIG. 4A. The member set shown in FIG. 4B includes the first member 400-1 and the second member 400-2 as described above with reference to FIG. 4A, and processes the feed solution 402 to separate the components 404 and provide the gas 406 as described above with reference to FIG. 4A. However, in contrast to the structure and operation of member set of FIG. 4A, the first member 400-1 and the second member 400-2 are offset, such that the feed solution 402 and the permeate flow primarily laterally (shown by arrow 408) through the first member 400-1 and the second member 400-2. The first member 400-1 and the second member 400-2 may be offset by 1 mm to 30 mm. Because of the offset, the first member 400-1 may not be directly aligned with the second member 400-2, and/or may not be in complete contact with the second member 400-2. "Primarily laterally" as used herein means that between of the permeate flows laterally, while the remainder flows vertically.

Figure 5:
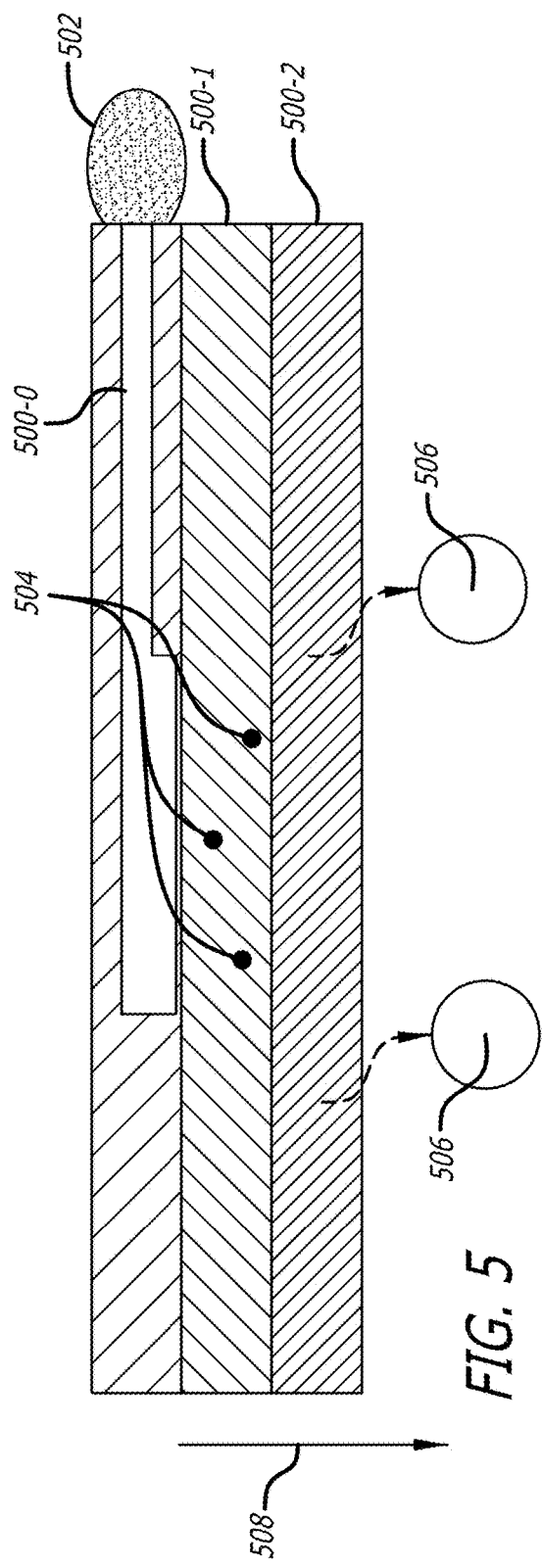
FIG. 5 illustrates an application of a feed solution to a member set of a sensing cartridge, where the member set includes a zero member.

FIG. 5 illustrates an application of a feed solution to a member set of a sensing cartridge, where the member set includes a zero member. The member set includes a first member 500-1 and a second member 500-2, which may correspond to the first member 400-1 and the second member 400-2 described above with reference to FIG. 4A, and processes a feed solution 502 to separate components 504 and provide gas 506 as described above with reference to FIG. 4A. However, in contrast to the structure and operation of the member set of FIG. 4A, a zero member 500-0 is associated with or coupled to the first member 500-1. As an example, the zero member 500-0 is a microfluidic member. The feed solution 502 is applied to and placed in fluid communication with the zero member 500-0. The zero member 500-0 is configured to enable transport of the feed solution 502 to the first member 500-1 through a microfluidic structure with a channel diameter of less than 2,000 µm.

While the feature of a zero member is described within the context of a sensing cartridge having a two-member member set, a zero member may be included in other sensing cartridge configurations. For example, a zero member may be included in sensing cartridges having three-member member sets or four-member member sets, which are described below.

Figure 6:
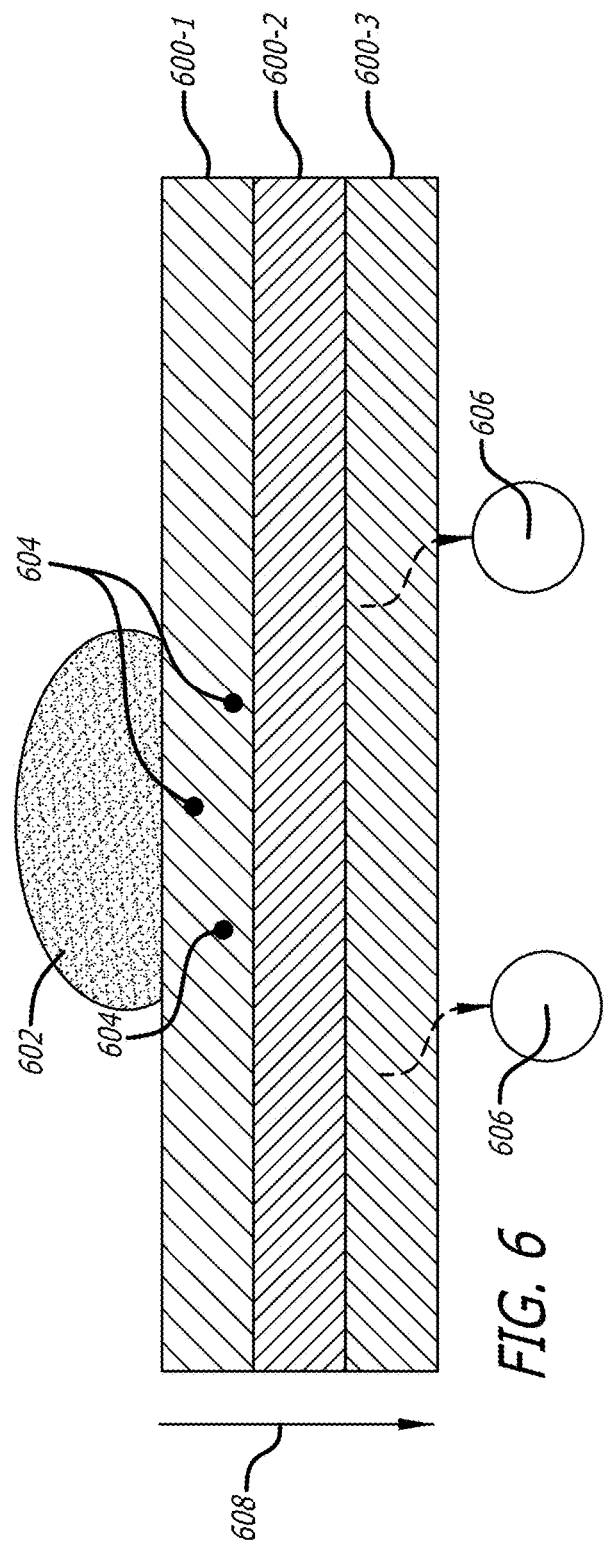
FIG. 6 illustrates an application of a feed solution to a member set of a sensing cartridge, where the member set includes three members.

FIG. 6 illustrates an application of a feed solution to a member set of a sensing cartridge, where the member set includes three members. The member set, which may represent the member set 305-1 of the sensing cartridge 300-2 of FIG. 3B, includes a first member 600-1, a second member 600-2, and a third member 600-3. The first member 600-1, the second member 600-2, and the third member 600-3 may respectively correspond to the first member 306-1, the second member 306-2, and the third member 306-3 described above with reference to FIG. 3B.

In operation, a feed solution 602 is applied to and placed in fluid communication with the first member 600-1. The first member 600-1 is configured to separate components 604 from the feed solution 602, and to retain the components 604 from the feed solution 602. The second member 600-2 is configured to wick a permeate from the first member 600-1, and to act on a constituent in the permeate to shift a phase equilibrium of the constituent to a gaseous state. The induced phase change by the second member 600-2 produces a gas 606 that is extracted from the permeate. The third member 600-3 is configured to prevent permeation of liquid permeate from the second member 600-2 while allowing gas to pass through. The third member 600-3 may be a gas diffusion member that prevents the liquid permeation. As an example, the gas 606 is produced in less than twenty minutes from introduction of the feed solution 602 to the first member 600-1. Arrow 608 represents a direction of flow of the feed solution 602 and permeate through the first member 600-1 and the second member 600-2 and the third member 600-3. The feed solution 602 and the permeate flow primarily vertically through the first member 600-1 and the second member 600-2 and the third member 600-3.

FIG. 7 illustrates an application of a feed solution to a member set of a sensing cartridge, where the member set includes four members. The member set, which may represent the member set 305-1 of the sensing cartridge 300-3 of FIG. 3C, includes a first member 700-1, a second member 700-2, a third member 700-3, and a fourth member 700-4. The first member 700-1, the second member 700-2, the third member 700-3, and the fourth member 700-4 may respectively correspond to the first member 306-1, the second member 306-2, the third member 306-3, and the fourth member 306-4 described above with reference to FIG. 3C.

In operation, a feed solution 702 is applied to and placed in fluid communication with the first member 700-1. The first member 700-1 is configured to separate components 704 from the feed solution 702, and to retain the components 704 from the feed solution 702. The second member 700-2 is configured to wick a permeate from the first member 700-1, and to act on a constituent in the permeate to shift a phase equilibrium of the constituent to a gaseous state. The induced phase change by the second member 700-2 produces a gas 706 that is extracted from the permeate. The third member 700-3 is configured to prevent permeation of liquid permeate from the second member 700-2 while allowing gas to pass through. The third member 700-3 may be a gas diffusion member that prevents the liquid permeation. The fourth member 700-4 is configured to respond to and/or capture the gas 706 from the third member 700-3. As an example, the gas 706 is produced in less than twenty minutes from introduction of the feed solution 702 to the first member 700-1. Arrow 708 represents a direction of flow of the feed solution 702 and permeate through the first member 700-1 and the second member 700-2 and the third member 700-3. The feed solution 702 and the permeate flow primarily vertically through the first member 700-1 and the second member 700-2 and the third member 700-3.

In an exemplary embodiment, the feed solution 702 applied to and placed in fluid communication with the first member 700-1 is whole blood. To separate plasma or serum (plasma/serum) from the whole blood, the first member 700-1 removes and retains the components 704. The components 704 may be cellular components and/or other components with a hydrodynamic radius greater than 0.01 µm. The second member 700-2 then wicks the plasma/serum from the first member 700-1 using capillary action and/or a chemical potential gradient. The capillary action and/or the chemical potential gradient may be the driving force(s) which enables quick drawing of the permeate (e.g., the plasma/serum) from the first member 700-1 into the second member 700-2. The second member 700-2 then acts on ammonium included in the plasma/serum to shift a phase equilibrium of the ammonium to the gas 706. The gas 706 is ammonia gas. The third member 700-3 prevents liquid permeation produced by the shift in the phase equilibrium of the ammonium to the ammonia gas. In addition, the ammonia gas (e.g., gas 706) diffuses through the third member 700-3 to trigger a response in the fourth member 700-4. The fourth member 700-4 responds to (e.g., via a colorimetric response) or captures the ammonia gas. In an embodiment, the fourth member 700-4 includes a gas responsive layer that has a proportional change in frequency in response to the quantity of ammonia present.

When whole blood with different ammonium concentrations is added as the feed solution 702, an accurate endpoint resolution exists between ammonium concentrations from 0 to 500 because the permeate from which the ammonium is measured may not contain erythrocytes, leukocytes, and/or thrombocytes as these cells are retained by the first member 700-1. If exposed to a highly alkaline solution, cell walls will degrade and (all) contained ions, including ammonium, will be released into the feed solution 702 or the permeate.

The embodiment of FIG. 7 may be superior to conventional enzymatic or photometric techniques for measuring ammonium because the conventional techniques may require the plasma/serum be separated from red blood cells in the whole blood through centrifugation before the measurement. As such, inaccurate measurements may result from significant variability within and across clinical labs in time from collecting a blood sample from a patient, to separating the serum/plasma through centrifugation, to measuring with a clinical laboratory instrument. By using an on-board membrane separation of red blood cells in the feed from plasma in the permeate using the first member 700-1, separation occurs more quickly than separation of the red blood cells from the plasma through centrifugation separation in the clinical lab. Additionally, separation by the first member 700-1 and wicking by the second member 700-2 may be significantly faster than conventional techniques which use a cation selective membrane to transport ions out of blood through a dense cation exchange membrane.

When deionized water, water treatment plant effluent, and water treatment plant effluent spiked with ammonium are added as the feed solution 702, there may be an improved endpoint resolution between ammonium concentrations from 0 µM to 200 µM (described in further detail with reference to FIG. 21A). Additionally, bacteria (described in further detail with reference to FIG. 23) commonly found in water treatment plant effluent are retained by the first member 700-1 and are not present in the permeate. When fresh human urine is added as the feed solution 702, there may be an improved endpoint resolution between different ammonium concentrations (described in further detail with reference to FIG. 21A) because the ammonium concentration is directly measured and not inferred.

FIG. 8 illustrates an application of a feed solution to a member set of a sensing cartridge, where the member set includes three members with different sizes. The member set may represent an alternate embodiment of the member set of FIG. 6. The member set shown in FIG. 8 includes a first member 800-1, a second member 800-2, and a third member 800-3, which may respectively correspond to the first member 600-1, the second member 600-2, and the third member 600-3 of the member set described with reference to FIG. 6, and processes a feed solution 802 to separate components 804 and provide gas 806 as described above with reference to FIG. 6. However, in contrast to the structure of the member set of FIG. 6, the first member 800-1, the second member 800-2, and the third member 800-3 have different dimensions. In an embodiment, the second member 800-2 and the third member 800-3 have dimensions between 50% and 150% of dimensions of the first member. For example, dimensions of the second member 800-2 are within 50% of the dimensions of the first member 800-1, and dimensions of the third member 800-3 are within 150% of the dimensions of the first member 800-1. By using members with different dimensions, leakage of fluid around the edges of the members may be prevented.

While the feature of different sized members is described within the context of a sensing cartridge having three-member member set, different sized members may be included in other sensing cartridge configurations. For example, sensing cartridges having two-member member sets or four-member member sets, such as described above with reference to FIGS. 4A, 4B, and 7, may have different sized members.

Figure 9:
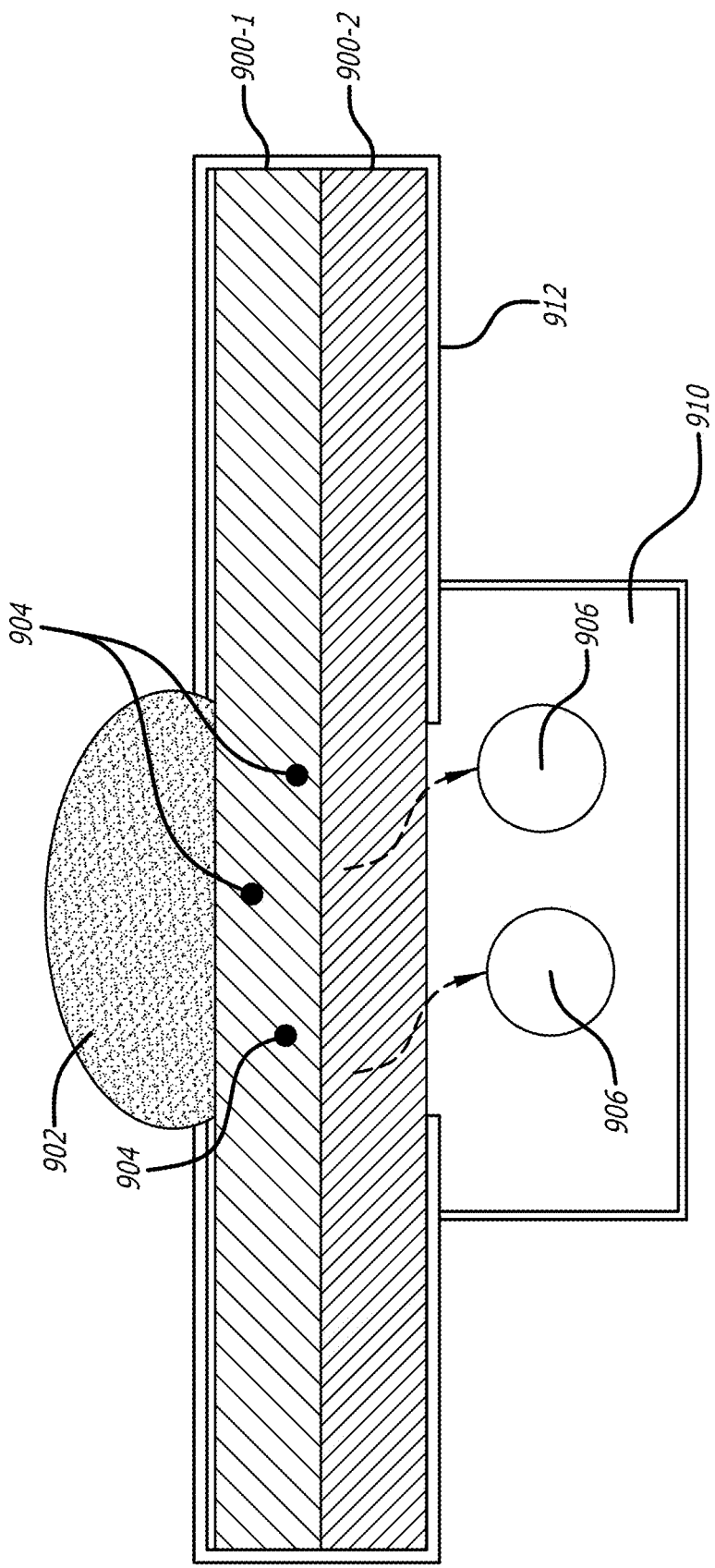
FIG. 9 illustrates a cross section of a sensing cartridge that is coupled to a gas detecting member.

FIG. 9 illustrates an application of a feed solution 902 to a sensing cartridge that includes a gas detecting member 910 coupled to a member housing 912. The member housing 912 includes a first member 900-1 and a second member 900-2, which may respectively correspond to the first member 400-1 and the second member 400-2 as described above with reference to FIG. 4A. The gas detecting member 910 is in fluid communication with the second member 900-2. As an example, the gas detecting member 910 is configured to detect the gas 906 from the second member 900-2. The gas detecting member 910 may detect the gas 906 via an electrochemical technique, a fuel cell, or an electrical, e.g., direct current, measurement technique. In an embodiment, the gas detecting member 910 changes in response to the presence of the gas 906 such that the change can be quantified.

Figure 10:
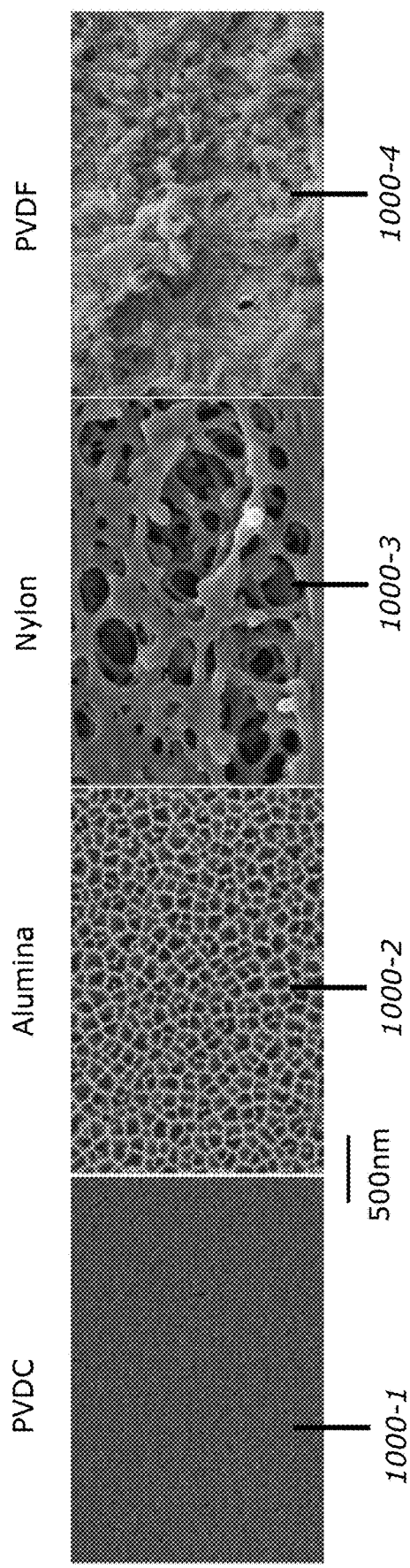
FIG. 10 depicts micrographs of feed solution accepting surfaces of membranes for a first member of a sensing cartridge.

FIG. 10 depicts micrographs of feed solution accepting surfaces of membranes for a first member of a sensing cartridge. The micrographs of membranes shown in FIG. 10 may represent membranes for a first member 306-1 of a sensing cartridge 300-1, such as shown in FIG. 3A. A first micrograph 1000-1 is a Polyvinylidene dichloride (PVDC) membrane. A second micrograph 1000-2 is an alumina membrane. A third micrograph 1000-3 is a nylon membrane. A fourth micrograph 1000-4 is a Polyvinylidene fluoride (PVDF) membrane. Although four micrographs of the feed solution accepting surfaces of the membranes for the first member are shown, the feed solution accepting surfaces of the membranes are not limited to those shown in FIG. 10.

The membranes may be described as a skin-like film which acts as a barrier or container wall, usually in the form of a permeable septum or a semipermeable septum. Constituents vary in their ability to diffuse through or to wet the membrane. The driving force for transport within the membrane may be determined by a concentration gradient of a solute, applied pressure, and/or chemical potential differences. Transport mechanisms through membranes can be convective flow through open pores, diffusion through solid phases, or a combination thereof.

A semipermeable membrane is a skin-like film which serves to define a barrier or container wall to at least one constituent of a solution or colloidal suspension. In an embodiment, "colloidal" may refer to a state of fine division of a material dispersed throughout a liquid almost to a point of a true solution that is difficult to filter and/or cause to settle. The semipermeable membrane allows at least one other constituent to pass through via a mechanism which may include but goes beyond mere physical straining, and which mechanism is in part due to differences in behavior of the constituents of the solution or suspension with respect to the material of the semipermeable membrane. "Suspension" may refer to a liquid carrying throughout its volume in extremely fine subdivision, an insoluble substance (solid or another liquid) which will not settle under gravity nor can be filtered without special treatment such as addition of chemical agents.

Other examples of a membrane for a first member include polysulfone-based materials and polysulfone-based derivatives, cellulose-based materials and cellulose-based derivatives, polyethylene materials and polyethylene derivatives, polypropylene materials and polypropylene derivatives, polymethyl methacrylate materials and polymethyl methacrylate derivatives, polyvinyl alcohol materials and polyvinyl alcohol derivatives, ethylene vinyl-alcohol materials and ethylene vinyl-alcohol derivatives, glass-fibers and glass-fiber derivatives, polyethersulfone materials and polyethersulfone derivatives, carbon-based materials and carbon-based derivatives, polyacrylonitrile materials, ceramics, anodized alumina, silica, and a combination of multiple organic and inorganic materials.

Figure 11:
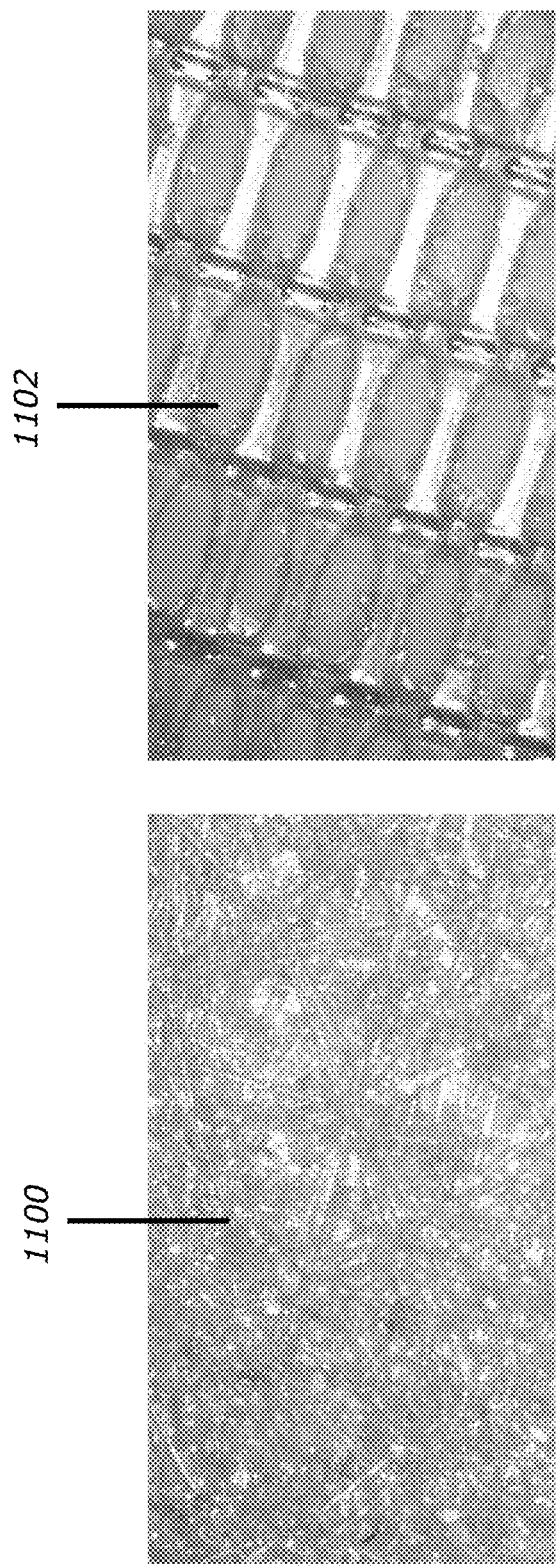
FIG. 11 depicts optical images of a nonwoven second member and a woven second member of a sensing cartridge.

FIG. 11 depicts optical images of a nonwoven second member 1100 and a woven second member 1100 of a sensing cartridge. The nonwoven second member 1100 and/or the woven second member 1102 shown in FIG. 11 may be for a second member 306-2 of a sensing cartridge 300-1, such as shown in FIG. 3A.

FIG. 12 is a table 1200 of permeate wicking properties of a second member of a sensing cartridge. The permeate wicking properties may be for a second member 306-2 of a sensing cartridge 300-1, such as shown in FIG. 3A. The table 1200 includes six columns, implemented as column 1, column 2, column 3, column 4, column 5, and column 6. Column 1 indicates a type of material. Column 2 indicates an average pore size of the material (in µm). Column 3 indicates an average percentage of permeate wicked into the second member from a first member (e.g., first member 306-1 of a sensing cartridge 300-1, such as shown in FIG. 3A) when 10 microliters (μL) of whole blood is applied to and placed in fluid communication with the first member. Column 4 indicates the standard deviation from an average of triplicate measurements for Column 3. Column 5 indicates an average percentage of permeate wicked into the second member from the first member when 10 μL of urine is applied to and placed in fluid communication with the first member. Column 6 indicates the standard deviation from an average of triplicate measurements for the average in Column 5.

Figures 13, 14:
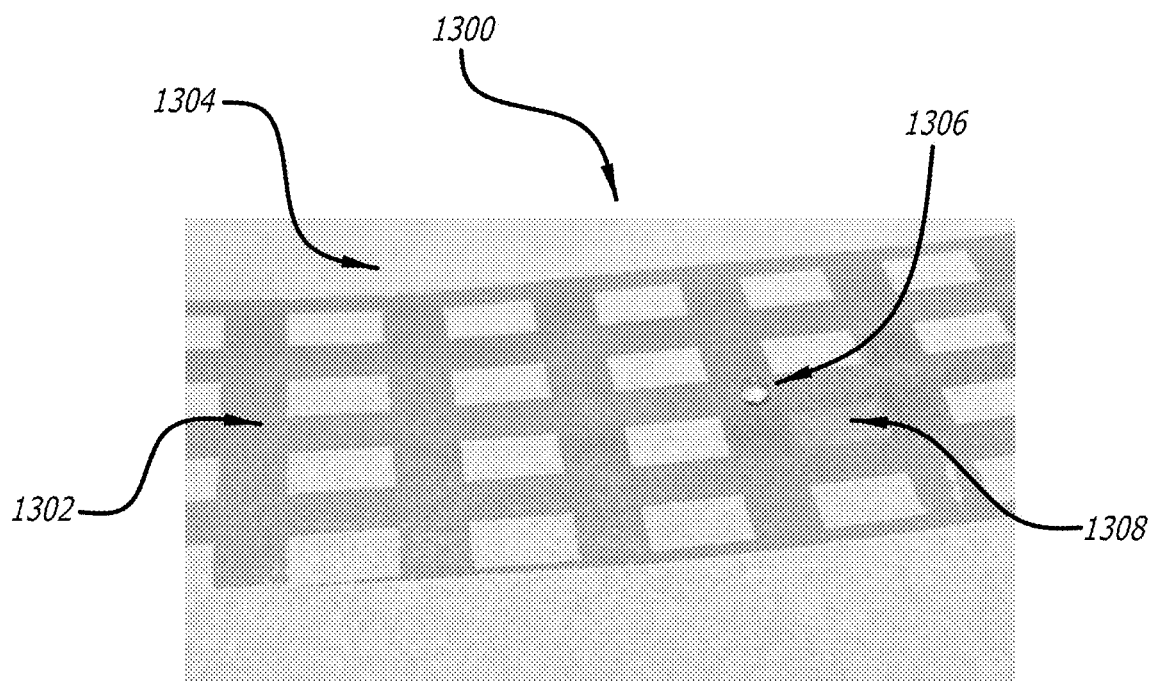
FIG. 13 depicts a second member of a sensing cartridge with hydrophobic patterning and hydrophilic patterning.
FIG. 14 is a table of properties and gas diffusion times of a third member of a sensing cartridge.

FIG. 13 depicts an example of a second member 1300 of a sensing cartridge with hydrophobic patterning 1302 and hydrophilic patterning 1304. The second member 1300 may be an embodiment of second member 306-2 of a sensing cartridge 300-1, such as shown in FIG. 3A. In an embodiment, the second member 1300 is a porous cellulosic paper with a thickness of 210 μm and a pore size of 8 μm. The hydrophobic patterning 1302 may be printed onto the second member 1300 following standard printing techniques from a printing solution of RapidCure white diluted by 50%. A first arrow 1306 indicates a drop of deionized water on the hydrophobic patterning 1302 that was not absorbed by the second member 1300. A second arrow 1308 indicates a drop of deionized water on the hydrophilic patterning 1304 that was absorbed by the second member 1300.

FIG. 14 is a table 1400 of properties and gas diffusion times of a third member of a sensing cartridge. The properties and the gas diffusion times may be for third member 306-3 of a sensing cartridge 300-3, such as shown in FIG. 3C. The table 1400 includes four columns, implemented as column 1, column 2, column 3, and column 4. Column 1 indicates a type of membrane of the third member. Column 2 indicates an average pore size of the membrane (in μm). Column 3 indicates an average thickness of the membrane (in μm). Column 4 indicates and average time (in seconds) for 50% of a gas to diffuse through the third member.

Figure 15:
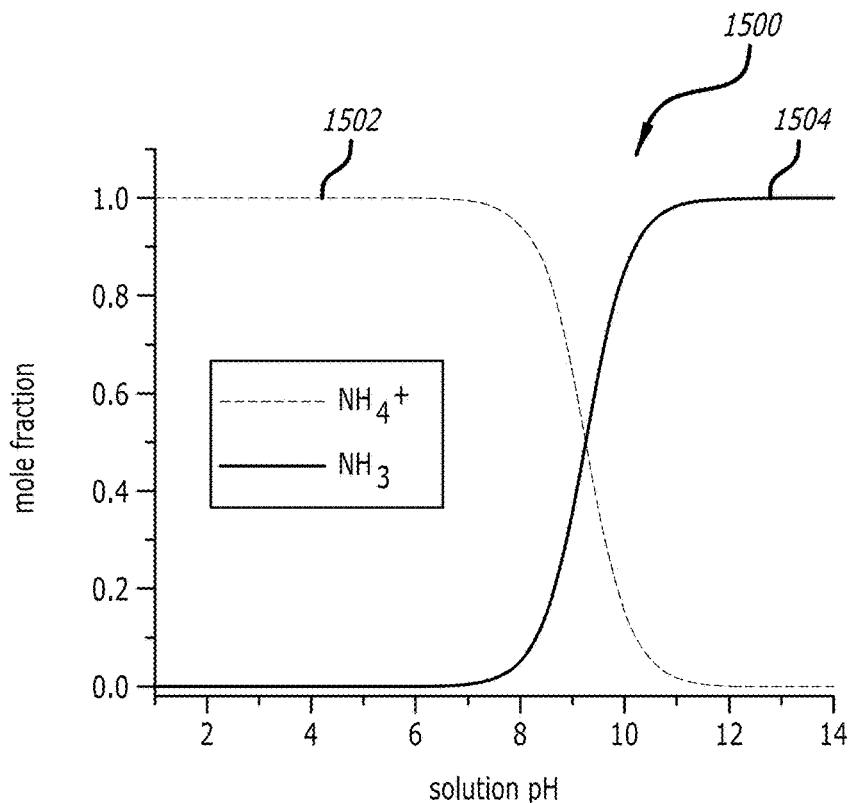
FIG. 15 depicts a graph of a phase equilibrium between ammonium ($NH_4^+$) and ammonia ($NH_3$).

FIG. 15 depicts a graph 1500 of a phase equilibrium between ammonium ($NH_4^+$) 1502 and ammonia ($NH_3$) 1504. An x-axis of the graph 1500 indicates a solution pH value. A y-axis of the graph 1500 indicates a mole fraction. The ammonium 1502 and the ammonia 1504 indicate a mole fraction of the ammonium and the ammonia, respectively. In an embodiment, the phase equilibrium between the ammonium 1502 and the ammonia 1504 is a known chemical equilibrium between ammonium ions and ammonia gas as a function of the pH of the liquid. The phase equilibrium is related to how the concentration of a base or an alkaline is selected for a conversion layer (e.g., a second member) of a sensing cartridge.

Figure 16:
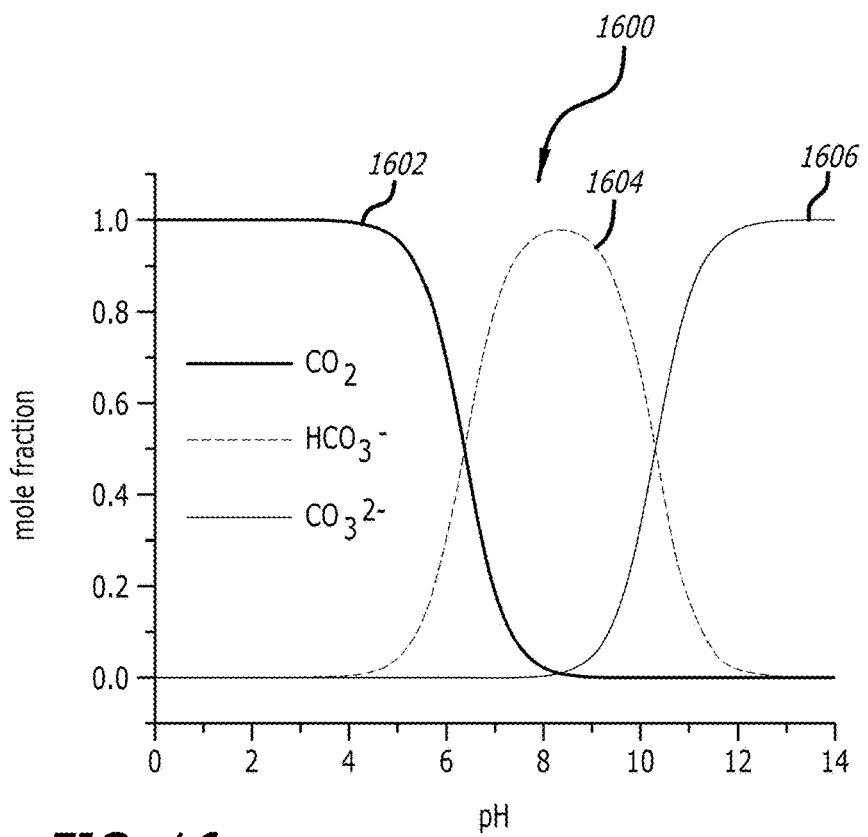
FIG. 16 depicts a graph of a phase equilibrium between carbon dioxide ($CO_2$), bicarbonate ($HCO_3^-$), and carbonate ($CO_3^{2-}$).

FIG. 16 depicts a graph 1600 of a phase equilibrium between carbon dioxide ($CO_2$) 1602, bicarbonate ($HCO_3^-$) 1604, and carbonate ($CO_3^{2-}$) 1606. An x-axis of the graph 1600 indicates a pH value. A y-axis of the graph 1600 indicates a mole fraction value. The carbon dioxide 1602, the bicarbonate 1604, and the carbonate 1606 are mole fractions of carbon dioxide, bicarbonate, and carbonate, respectively, as a function of pH. In an embodiment, the phase equilibrium between the carbon dioxide 1602, the bicarbonate 1604, and the carbonate 1606 is a known chemical equilibria.

Figure 17:
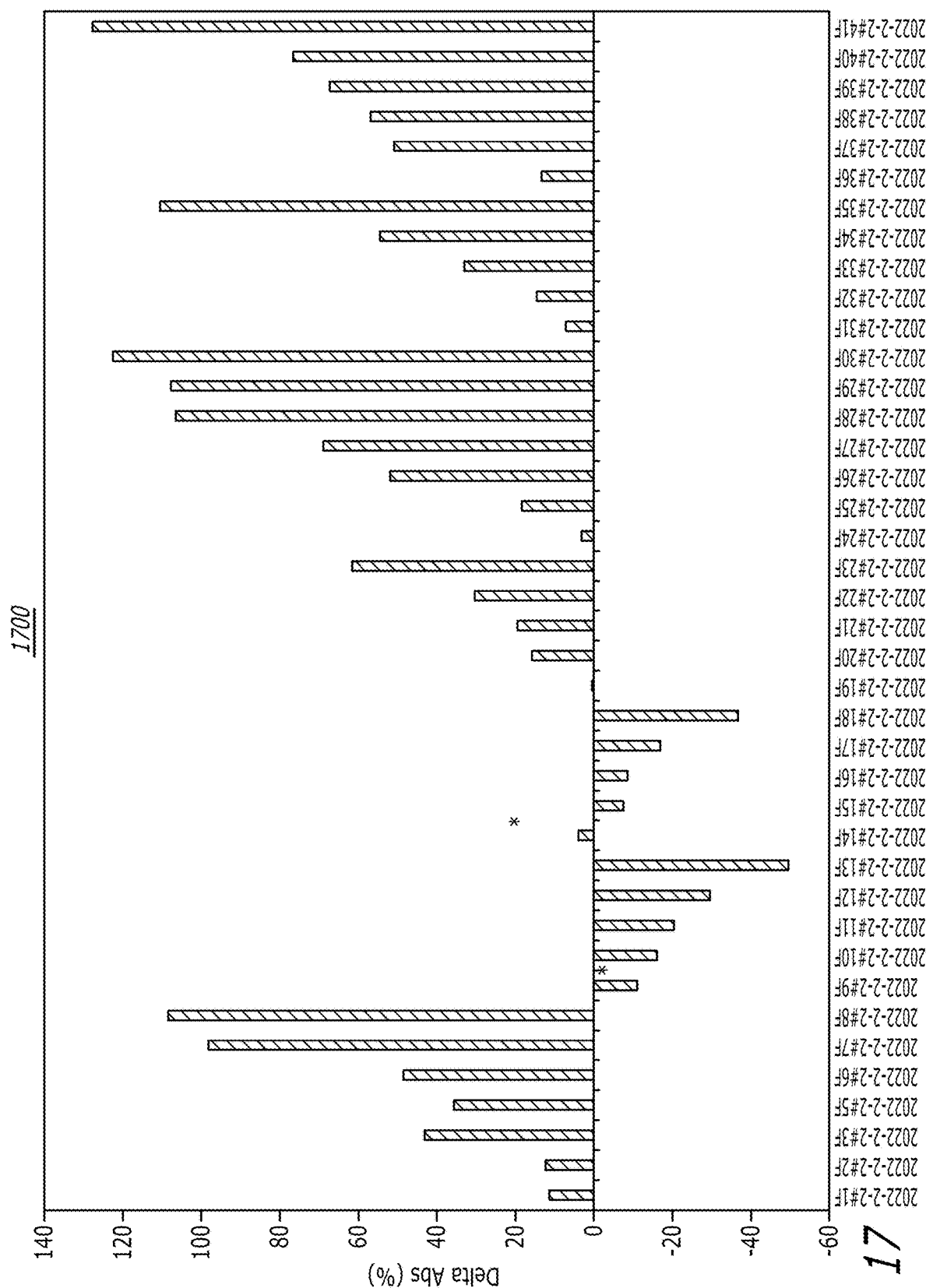
FIG. 17 depicts a graph of a frequency response of gas sensing layers for 3.4 parts per million (ppm) ammonia as a function of a molar ratio between a polymer and an indicator.

FIG. 17 depicts a graph 1700 of a frequency response of gas sensing layers for 3.4 parts per million (ppm) ammonia as a function of a molar ratio between a polymer and an indicator. An x-axis of the graph 1700 indicates a ppm value of ammonia. A y-axis of the graph 1700 indicates Delta Abs (%). In an embodiment, the gas sensing layers are included in a fourth member (e.g., fourth member 306-4 of a sensing cartridge 300-3, such as shown in FIG. 3C) of a sensing cartridge.

In an embodiment, the graph 1700 shows a change in absorbance in a red component of different sensor chemistry compositions of the fourth member in response to air with 3 ppm ammonia gas. As an example, a higher value may correspond to a larger sensor response to ammonia and overall better sensor sensitivity.

Figure 18:
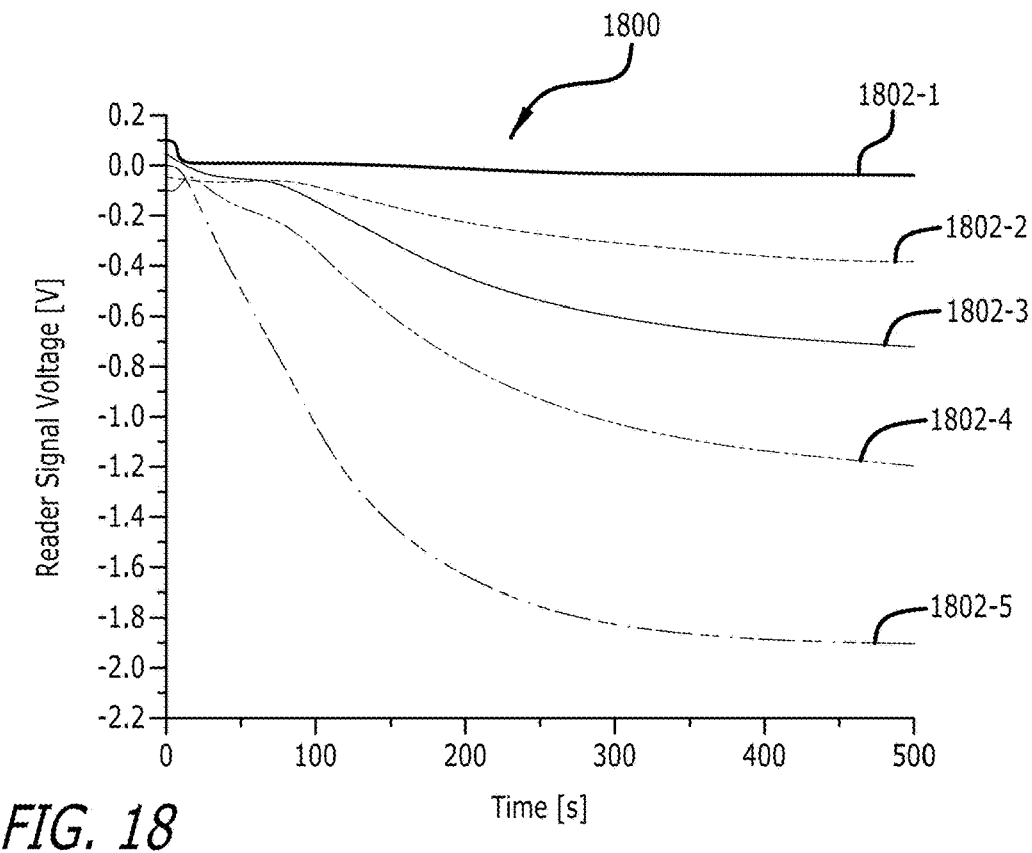
FIG. 18 depicts a graph of optoelectronic reader measurement responses to sensing cartridges with different constituent concentrations.

FIG. 18 depicts a graph 1800 of optoelectronic reader measurement responses to sensing cartridges with different constituent concentrations. The optoelectronic reader responses may be produced by optoelectronic reader 102 (FIG. 1) and represent changes in reader signal measurements as a function of time. The x-axis of the graph 1800 indicates time in seconds (s). The y-axis of the graph 1800 indicates a reader signal measurement in voltage (V). In an embodiment, the optoelectronic reader responses are photodiode responses to sensing cartridges that include members for liquid separation, gas extraction, gas diffusion, and gas response. A 10 μL feed solution was applied to 15 different sensing cartridges. A first line 1802-1 represents the photodiode response to a feed solution of whole blood. A second line 1802-2 represents the photodiode response to a feed solution of whole blood with an added 50 μM ammonium. A third line 1802-3 represents the photodiode response to a feed solution of whole blood with an added 100 μM ammonium. A fourth line 1802-4 represents the photodiode response to a feed solution of whole blood with an added 200 μM ammonium. A fifth line 1802-5 represents the photodiode response to a feed solution of whole blood with an added 500 μM ammonium.

With reference to FIG. 18, the graph 1800 shows raw voltage signal curves based on measurements by a sensing photodiode of an optoelectronic reader over 500 seconds for different ammonium compositions of whole blood added to a sensing cartridge with four members. The raw voltage signals are processed by an algorithm stored in firmware of the optoelectronic reader to provide an ammonia measure or value. To this end, the algorithm is configured to determine a measurement change, e.g., a voltage change, from the raw voltage signals, and to convert the voltage change into an ammonia measure based on unique calibration factors. The ammonia measure or value may be an amount or concentration. The unique calibration factors, which are described below with reference to FIG. 19, may be determined for a sensing cartridge during manufacturing of that sensing cartridge.

The ammonia measure or value determined by the algorithm may be provided to a user of the optoelectronic reader. For example, the value may be displayed on a display of the reader or communicated by the reader to a user device, e.g., mobile phone, where the value is displayed.

Figure 19:
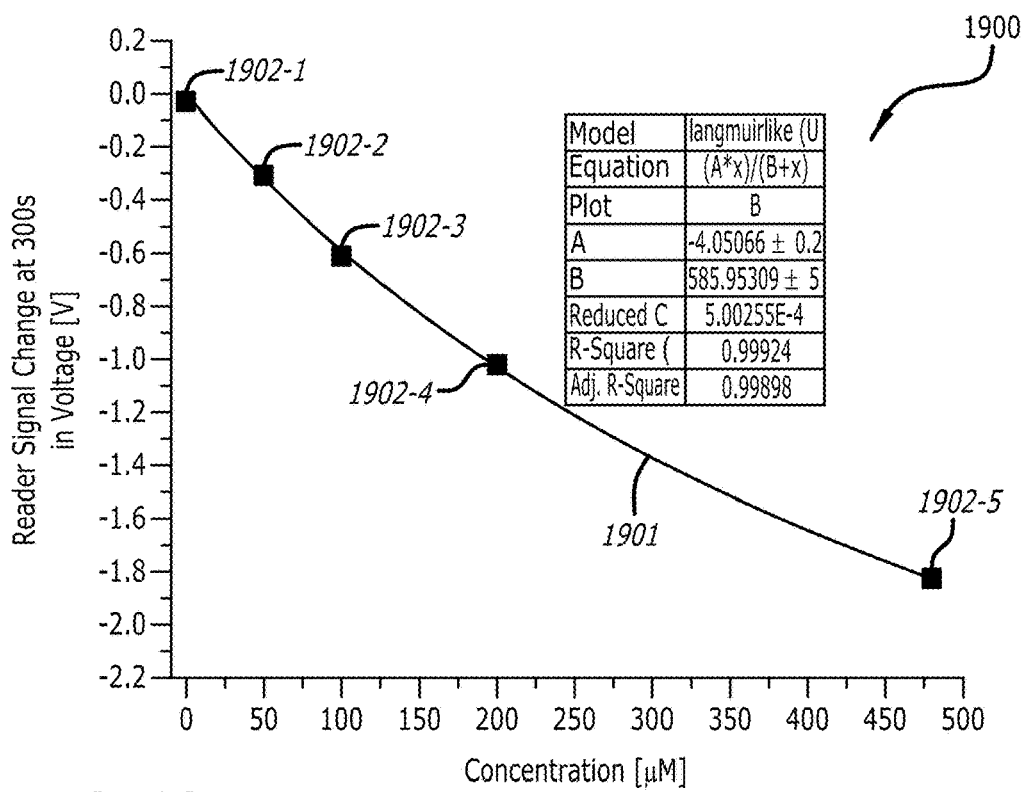
FIG. 19 depicts a graph of a calibration curve for an optoelectronic reader at 300 seconds (s) after adding a feed solution to a sensing cartridge.

FIG. 19 depicts a graph 1900 of a calibration curve 1901 for an optoelectronic reader at 300 s after adding a feed solution to a sensing cartridge. The x-axis of the graph 1900 indicates a constituent concentration (in micromolar (μM)). The y-axis of the graph 1900 indicates a reader signal change at 300 s (in V). The graph 1900 includes five constituent concentrations, which correspond to the feed solutions described with reference to FIG. 18. A first constituent concentration 1902-1 corresponds to a feed solution of whole blood (first line 1802-1 in FIG. 18). The change in voltage measured by the optoelectronic reader at 300 s for the first constituent concentration 1902-1 is substantially zero, which is consistent with the substantially "flat" first line 1802-1. A second constituent concentration 1902-2 corresponds to a feed solution of whole blood with an added 50 μM of ammonium (second line 1802-2 in FIG. 18). The change in voltage measured by the optoelectronic reader at 300 s for the second constituent concentration 1902-2 is approximately −0.3, which is consistent with the curve of the second line 1802-2. A third constituent concentration 1902-3 corresponds to a feed solution of whole blood with an added 100 μM ammonium (third line 1802-3 in FIG. 18). The change in voltage measured by the optoelectronic reader at 300 s for the third constituent concentration 1902-3 is approximately −0.6, which is consistent with the curve of the third line 1802-3. A fourth constituent concentration 1902-4 corresponds to a feed solution of whole blood with an added 200 μM ammonium (fourth line 1802-4 in FIG. 18). The change in voltage measured by the optoelectronic reader at 300 s for the fourth constituent concentration 1902-4 is approximately −1.0, which is consistent with the curve of the fourth line 1802-4. A fifth constituent concentration 1902-5 corresponds to a feed solution of whole blood with an added 500 μM ammonium (fifth line 1802-5 in FIG. 18). The change in voltage measured by the reader at 300 s for the fifth constituent concentration 1902-5 is approximately −1.9, which is consistent with the curve of the fifth line 1802-5.

With reference to FIG. 19, the graph 1900 shows the calibration curve 1901 for the different constituent concentrations of FIG. 18. In an embodiment, the calibration curve 1901 is a Langmuir-like model fit to the data of points 1902-1, 1902-2, 1902-3, 1902-4, and 1902-5. The Langmuir-like model fit parameters are considered calibration coefficients and are stored in cartridge packaging. A software application may then extract the calibration coefficients from the cartridge packaging and send them to firmware of an optoelectronic reader where they are used to convert raw signals measured by the optoelectronic reader into an ammonia concentration that the application to reports to a user.

Figure 20:
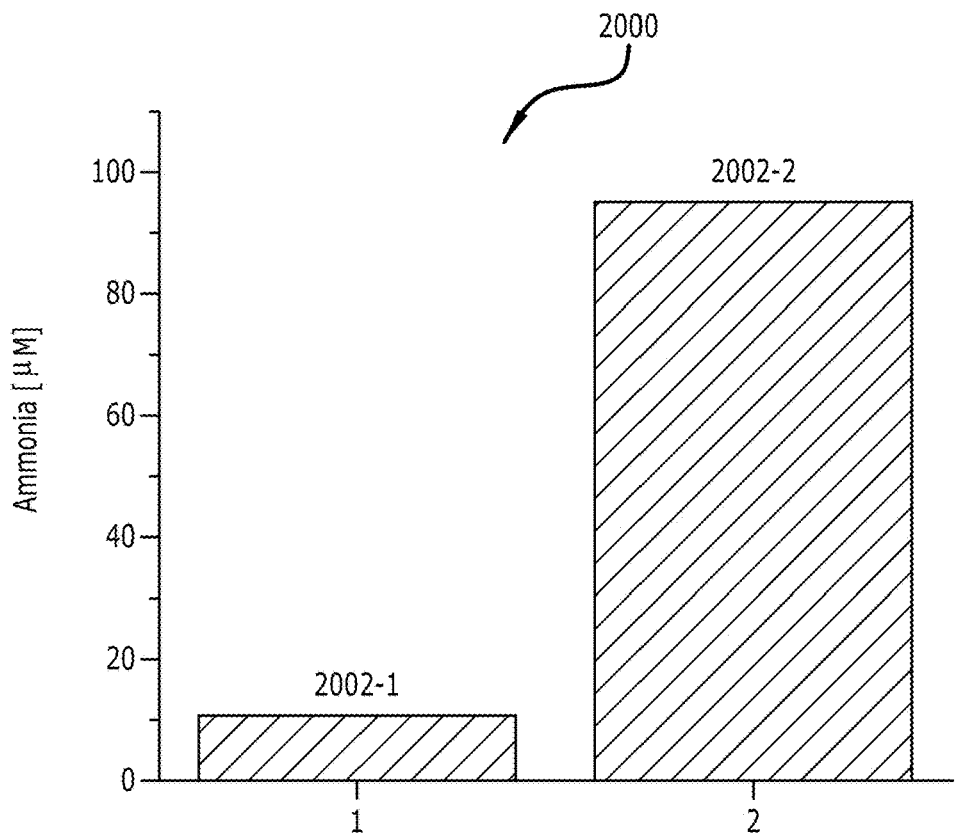
FIG. 20 depicts a graph of ammonia measurements.

FIG. 20 depicts a graph 2000 of ammonia levels or values. An x-axis of the graph 2000 indicates plasma samples. A y-axis of the graph 2000 indicates ammonia (in μM) from the plasma samples. A first plasma sample 2002-1 is alkalinized plasma. A second plasma sample 2002-2 is plasma separated from whole blood after the whole blood is alkalinized with 6 molar (M) potassium carbonate. In an embodiment, the second plasma sample 2002-2 is direct alkalinization of 350 μL whole blood with 175 μL of 6 M potassium carbonate. In such an embodiment, the direct alkalinization releases extra ammonium from cellular and other components in the whole blood. As such, the direct alkalinization of the whole blood may result in a falsely elevated plasma ammonia measurement as a result of the alkalinization on complex living tissue of the whole blood.

Figure 21A:
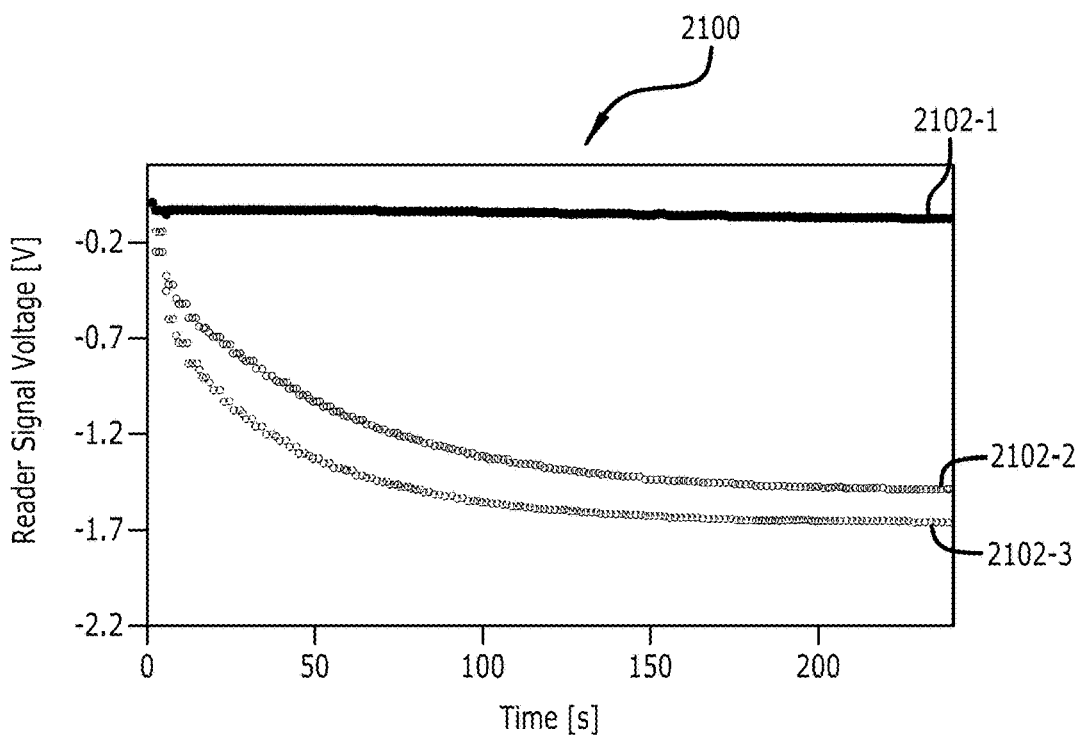
FIG. 21A depicts a graph of optoelectronic reader measurement responses to a feed solution of effluent.

FIG. 21A depicts a graph 2100 of optoelectronic reader measurement responses to a feed solution of effluent, where the responses represent changes in reader signal measurements as a function of time. The optoelectronic reader responses may be produced by optoelectronic reader 102 (FIG. 1). In an embodiment, the feed solution of effluent is a feed solution of effluent that is added to a sensing cartridge with two sets of four members (e.g., sensing cartridge 300-5 in FIG. 3E).

The x-axis of the graph 2100 indicates time in seconds (s). The y-axis of the graph 2100 indicates a reader signal measurement in voltage. A first line 2102-1 represents a signal for deionized water control. A second line 2102-2 represents a signal for an Arizona effluent brine concentrate. A third line 2102-3 represents a signal for an Arizona effluent brine concentrate with an added 200 μM ammonium.

Figure 21B:
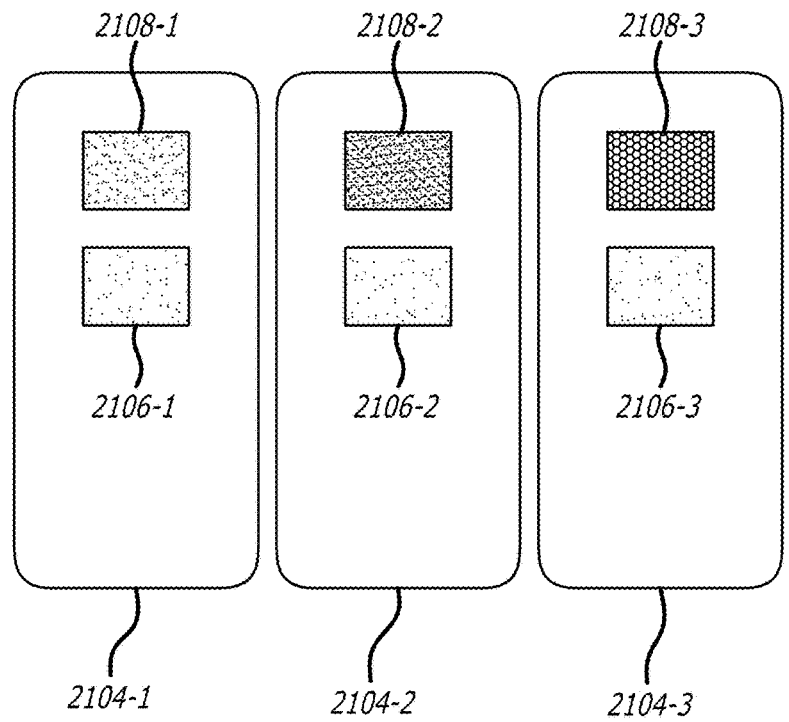
FIG. 21B depicts sensing cartridge property responses to the feed solution of effluent of FIG. 21A.

FIG. 21B depicts sensing cartridge property responses to the feed solution of effluent of FIG. 21A for a first sensing cartridge 2104-1, a second sensing cartridge 2104-2, and a third sensing cartridge 2104-3. Each of the sensing cartridges 2104-1, 2104-2, and 2104-3 includes a control window 2106-1, 2106-2, 2106-3 and a response window 2108-1, 2108-2, 2108-3. The sensing cartridges 2104-1, 2104-2, and 2104-3 may be embodiments of the sensing cartridge 300-5 describe above with reference to FIG. 3E, where each of the fourth members 306-4a, 306-4b is visible through a respective response window 2108-1, 2108-2, 2108-3 of the cartridge. The property response may be a change in color that is proportional to a quantity of diffused gas present in the sensing cartridge. The sensing cartridge property responses shown in FIG. 21B are at 300 seconds after application of a feed solution to the first sensing cartridge 2104-1, the second sensing cartridge 2104-2, and the third sensing cartridge 2104-3.

The control window 2106-1, 2106-2, 2106-3 is the same shade of green in each sensing cartridges 2104-1, 2104-2, and 2104-3. The first sensing cartridge 2104-1 depicts a response to deionized water control (which corresponds to the first line 2102-1 in FIG. 21A). The response window 2108-1 for the first sensing cartridge 2104-1 is a darker shade of green than the control window 2106-1. The second sensing cartridge 2104-2 depicts a response to an Arizona effluent brine concentrate (which corresponds to the second line 2102-2 in FIG. 21A). The response window 2108-2 for the second sensing cartridge 2104-2 is a darker shade of green than the response window 2108-1 for the first sensing cartridge 2104-1. The third sensing cartridge 2104-3 depicts a response to an Arizona effluent brine concentrate with an added 200 μM ammonium (which corresponds to the third line 2102-3 in FIG. 21A). The response window 2108-3 for the third sensing cartridge 2104-3 is a shade of blue.

Figure 22:
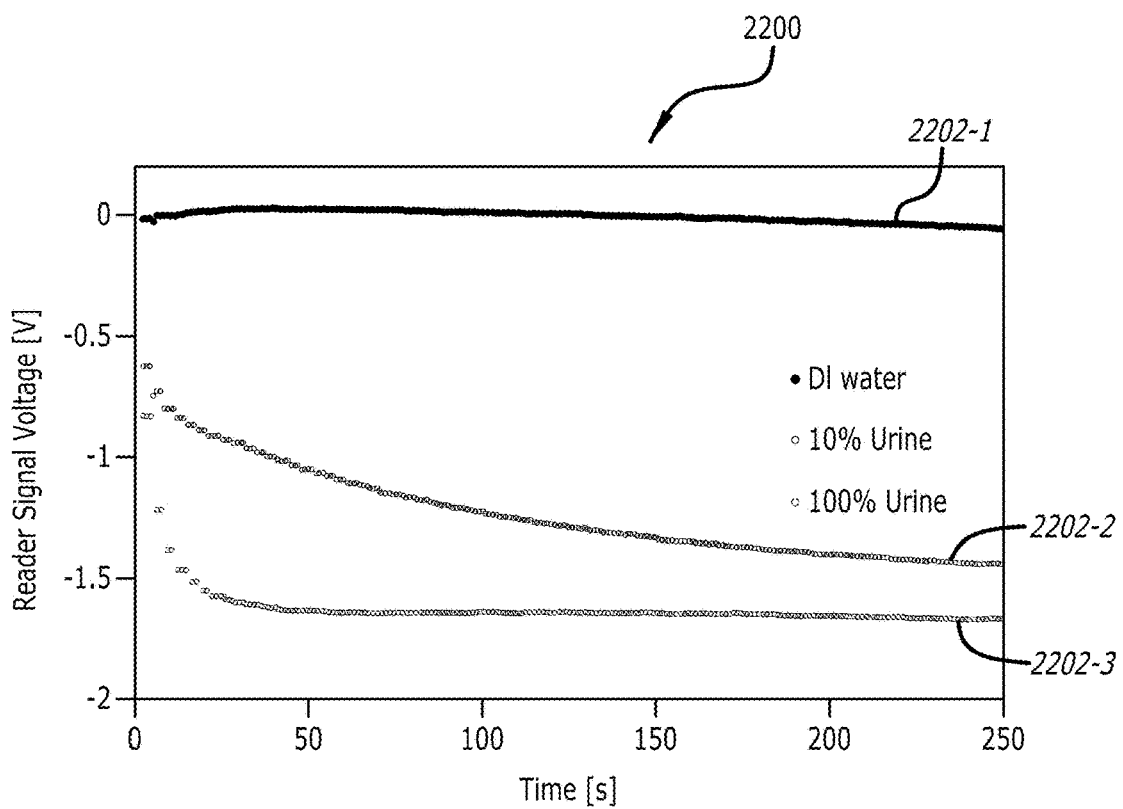
FIG. 22 depicts a graph of optoelectronic reader measurement responses to a feed solution of urine.

FIG. 22 depicts a graph 2200 of optoelectronic reader measurement responses to a feed solution of urine, where the responses represent changes in reader signal measurements as a function of time. The x-axis of the graph 2200 indicates time (in seconds). The y-axis of the graph 2200 indicates a reader signal measurement (in volts). A first line 2202-1 represents a signal for a feed solution of deionized water. A second line 2202-2 represents a signal for a feed solution of 10% urine. A third line 2202-3 represents a signal for a feed solution of 100% urine.

FIG. 23 is a table 2300 of cellular components of bodily fluids and of water. The table 2300 includes two columns, implemented as column 1 and column 2. Column 1 indicates types of cells found in bodily fluids and effluent. Column 2 indicates an average diameter of the types of cells in column 1 (in μm).

FIG. 24 is a table 2400 of phase change equilibriums for a plurality of species. The table 2400 includes three columns, implemented as column 1, column 2, and column 3. Column 1 indicates components of liquids that could be extracted. Column 2 indicates mechanisms to induce a phase change in the component of column 1. Column 3 indicates a species resulting after the phase change of constituent in column 1 with the mechanism in column 2.

Figure 25:
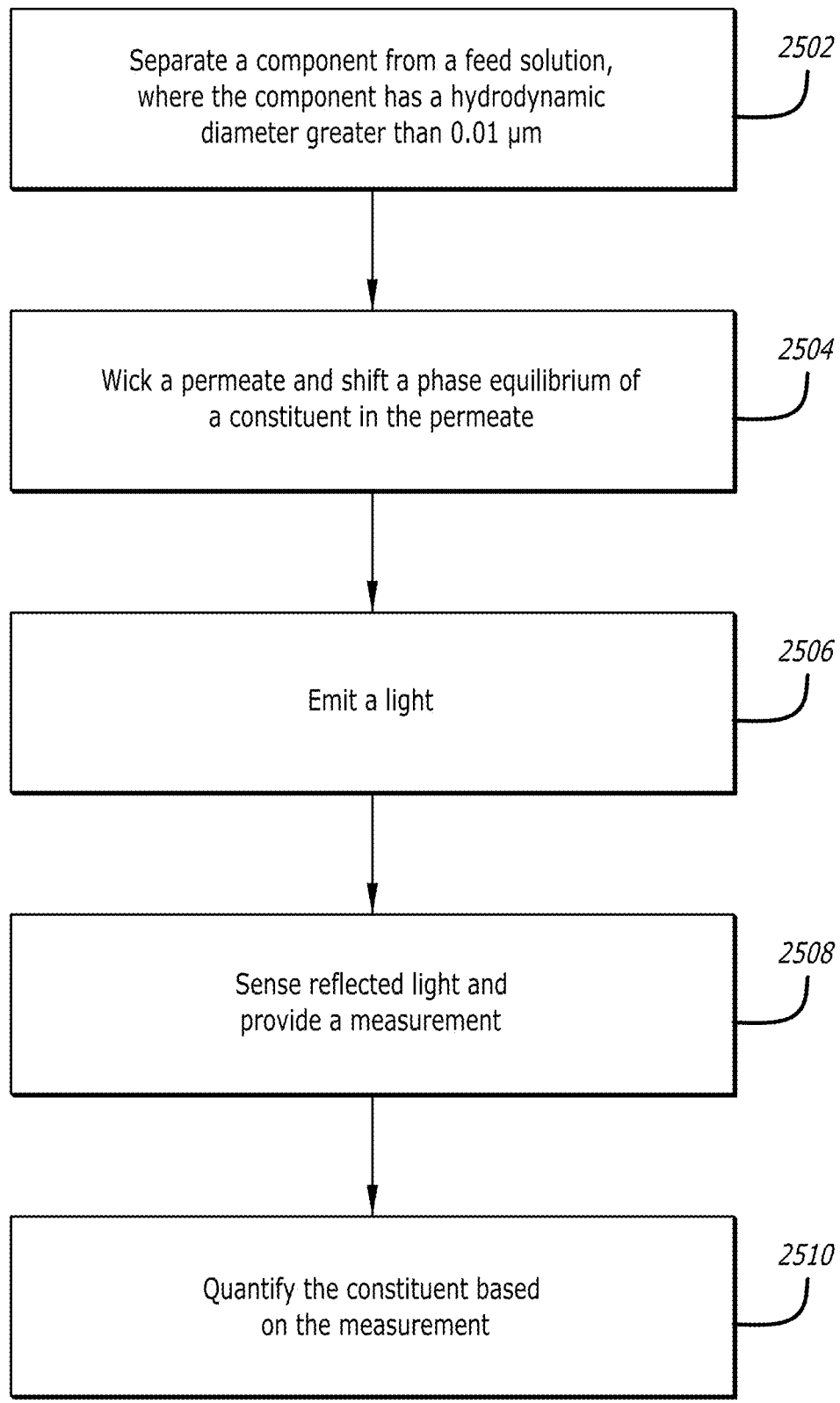
FIG. 25 is a flowchart of a method of deriving a permeate from a feed solution and quantifying a constituent of the feed solution.

FIG. 25 is a flowchart of a method of deriving a permeate from a feed solution and quantifying a constituent of the feed solution. The method may be enabled by the system 100 of FIG. 1, including an optoelectronic reader 200, such as described above with reference to FIGS. 2A and 2B, and a sensing cartridge 300-1 with a first member 306-1 and a second member 306-2, such as described above with reference to FIG. 3A.

At block 2502, the first member of the sensing cartridge separates a component from a feed solution, where the component has a hydrodynamic diameter greater than 0.01 μm.

At block 2504, the second member of the sensing cartridge wicks a permeate from the first member. In an embodiment, the second member also acts on a constituent in the permeate to shift a phase equilibrium of the constituent to a gaseous state.

Although not shown, a third member of the sensing cartridge optionally prevents liquid permeation produced by the shift in the phase equilibrium of the constituent to the gaseous state, and a fourth member optionally responds to diffused gas of the constituent. The third member and the fourth member may be such as described above with reference to FIGS. 3C and 3E.

At block 2506, the optoelectronic reader emits a light towards the sensing cartridge. In an embodiment, the optoelectronic reader includes a LED configured to emit the light towards the sensing cartridge.

At block 2508, the optoelectronic reader senses reflected light from the sensing cartridge and provides a measurement based on the reflected light. In an embodiment, the optoelectronic reader includes a sensing photodiode configured to sense the reflected light from the sensing cartridge and to provide a measurement based on the sensed light. In some embodiments, the measurement may correspond to raw measurements, e.g., voltage values, obtained over time. For example, as described above with reference to FIGS. 18, the optoelectronic reader may output a series of voltage values collected over a time period, e.g., 500 seconds. In some embodiments, the measurement may correspond to a change in a measurement, e.g., a voltage change, that occurred over time. For example, as described above with reference to FIGS. 19, the optoelectronic reader may output a voltage change value corresponding to the difference in the voltage measured at an initial time (at or just after time zero) and at 300 seconds.

At block 2510, a processor quantifies the constituent in the feed solution based on the measurement. In an embodiment, the optoelectronic reader includes a processor that is configured to derive a value corresponding to a concentration of a constituent in the feed solution. In another embodiment, the optoelectronic reader provides the measurement to a remote processor that is configured to derive a value corresponding to a concentration of a constituent in the feed solution.

In either case, the processor may be configured to derive a value corresponding to a concentration of a constituent in the feed solution based on the measurements, as described above with reference to FIG. 18. For example, in the case of a measure of ammonia in whole blood, a processor may be configured to execute a software application that processes measurements from the optoelectronic reader and outputs a value corresponding to the concentration of ammonia in the whole blood. As previously described, in such an example, a sensing cartridge of the optoelectronic reader contains fitting parameters (or calibration factors). In one embodiment, the fitting parameters are proportional to voltage change measured at 300 s. In another embodiment, the fitting parameters are based on derivatives of raw signals, which are described with reference to FIGS. 18, 21A, and 22.

With reference to FIG. 1, a system 100 for quantifying a constituent in a feed solution as describe above with reference to FIG. 25 includes a sensing cartridge 104 and an optoelectronic reader 102. The optoelectronic reader 102 is configured to receive and removably couple with the sensing cartridge 104 and to quantify the constituent in a feed solution based on reflected light from the sensing cartridge or to provide measurements for use in quantifying the constituent. To this end, and with additional reference to FIGS. 2A and 2B, the optoelectronic reader 102 includes a LED 214-1, 214-2 configured to emit a light towards the sensing cartridge 104, and a sensing photodiode 216-1, 216-2 configured to sense reflected light from the sensing cartridge and to provide a measurement based on the reflected light. A processor resident within the optoelectronic reader 102 is configured to quantify the constituent based on the measurement. Alternatively, the optoelectronic reader 102 is configured to communicate the measurement to a processor remote from the optoelectronic reader 102, wherein the remote processor is configured to quantify the constituent based on the measurement. The quantification may be a concentration of the constituent or an amount of the constituent, and may serve as a biomarker for purposes of monitoring patient conditions. To this end, quantifications (or biomarkers) may be obtained periodically, e.g., hourly, daily, weekly, and processed to detect a trend in the biomarker, and to tailor patient drug therapy accordingly.

In other embodiments, the reader 102 may be configured to quantify the constituent in the feed solution or to provide related measurements for use in quantifying the constituent based on sensing techniques other than optoelectronic. For example, the reader may quantify the constituent in the feed solution or provide related measurements based on electrochemical sensing by an electrochemical sensor or electrical sensing by an electrode sensor.

With reference to FIG. 3A, the sensing cartridge 300-1 may include a first member set 305-1 having a first member 306-1 and a second member 306-2 that is coupled to the first member. The first member 306-1 is configured to separate a component from a feed solution, where the component has a hydrodynamic diameter greater than 0.01 μm. The second member 306-2 is configured to wick a permeate from the first member 306-1 and to shift a phase equilibrium of a constituent in the permeate to a gaseous state.

With reference to FIG. 3B, the sensing cartridge 300-2 may include a first member set 305-1 having first member 306-1, a second member 306-2 coupled to the first member, and a third member 306-3 coupled to the second member. The first member 306-1 is configured to separate a component from a feed solution, where the component has a hydrodynamic diameter greater than 0.01 μm. The second member 306-2 is configured to wick a permeate from the feed solution, where the second member acts on a constituent in the permeate to shift a phase equilibrium of the constituent to a gaseous state. The third member 306-3 is configured to prevent liquid permeation produced by the shift in the phase equilibrium of the constituent to the gaseous state.

With reference to FIG. 3C, the sensing cartridge 300-3 may include a first member set 305-1 having a first member 306-1, a second member 306-2 coupled to the first member, a third member 306-3 coupled to the second member, and a fourth member 306-4 coupled to the third member. The first member 306-1 is configured to separate a component from a feed solution, where the component has a hydrodynamic diameter greater than 0.01 μm. The second member 306-2 is configured to wick a permeate from the feed solution, where the second member acts on a constituent in the permeate to shift a phase equilibrium of the constituent to a gaseous state. The third member 306-3 is configured to prevent liquid permeation produced by the shift in the phase equilibrium of the constituent to the gaseous state. The fourth member 306-4 is configured to respond to diffused gas of the constituent.

With reference to FIG. 3D, the sensing cartridge 300-4 may include a first member set 305-1 and a second member set 305-2, each having a first member 306-1a/b, a second member 306-2a/b coupled to the first member, and a third member 306-3a/b coupled to the second member. The first member 306-1a/b, the second member 306-2a/b, and the third member 306-3a/b may be configured as described above with reference to FIG. 3B.

With reference to FIG. 3E, the sensing cartridge 300-5 may include a first member set 305-1 and a second member set 305-2, each having a first member 306-1a/b, a second member 306-2a/b coupled to the first member, a third member 306-3a/b coupled to the second member, and a fourth member 306-4a/b coupled to the third member. The first member 306-1a/b, the second member 306-2a/b, the third member 306-3a/b, and the fourth member 306-4a/b may be configured as described above with reference to FIG. 3C.

Figure 26:
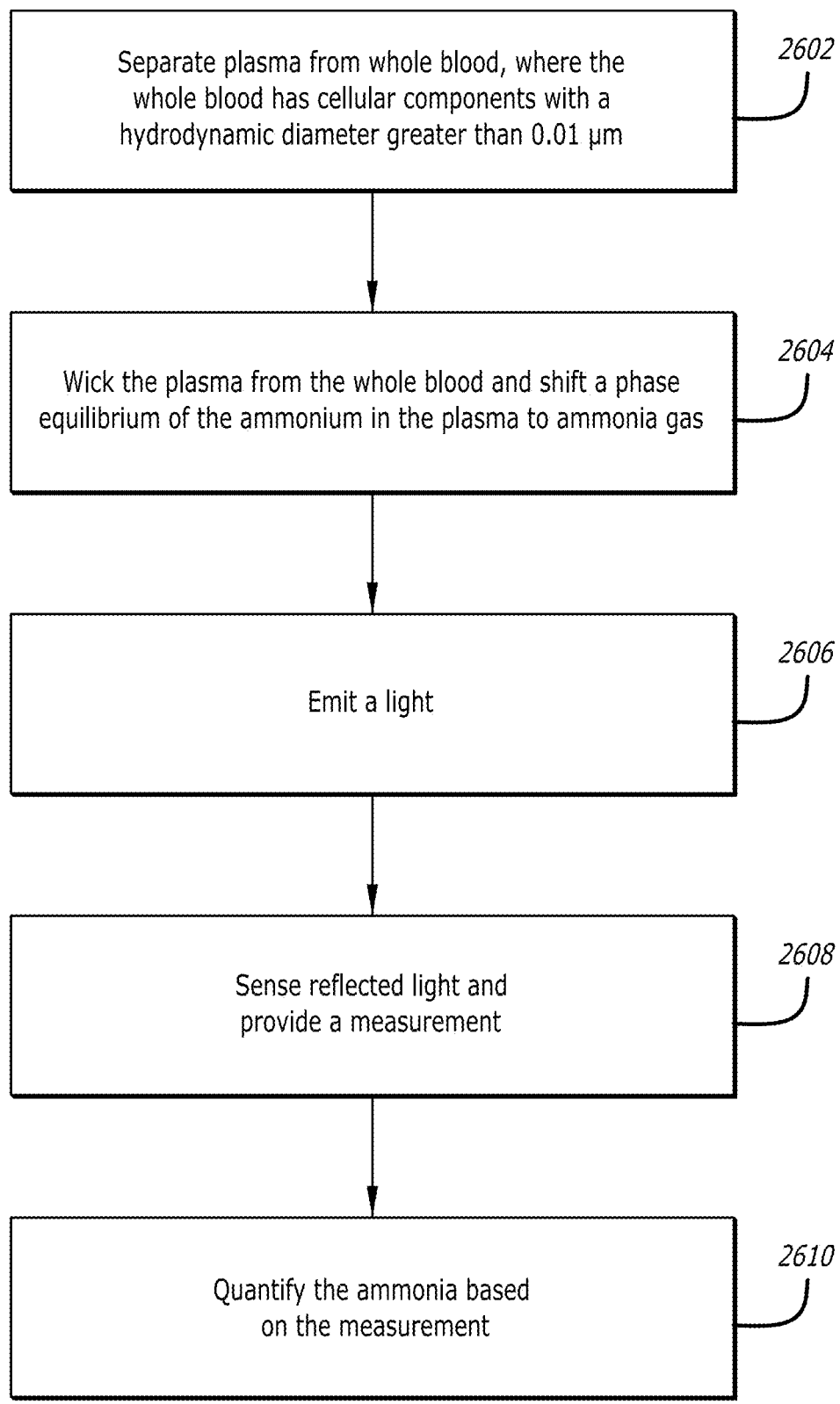
FIG. 26 is a flowchart of a method of deriving a plasma from whole blood and quantifying ammonia gas of the whole blood.

FIG. 26 is a flowchart of a method of deriving plasma from whole blood and quantifying ammonia gas of the whole blood. The method may be enabled by the system 100 of FIG. 1, including an optoelectronic reader 200, such as described above with reference to FIGS. 2A and 2B, and a sensing cartridge 300-1 with a first member 306-1 and a second member 306-2, such as described above with reference to FIG. 3A.

At block 2602, the first member of the sensing cartridge separates plasma from whole blood, where the whole blood has cellular components with a hydrodynamic diameter greater than 0.01 µm.

At block 2604, the second member of the sensing cartridge wicks the plasma from the whole blood, where the second member acts on ammonium in the plasma to shift a phase equilibrium of the ammonium to ammonia gas. In an embodiment, the second member also acts on ammonium in the plasma to shift a phase equilibrium of the ammonium to the ammonia gas.

Although not shown, a third member of the sensing cartridge optionally prevents liquid permeation produced by the shift in the phase equilibrium of the ammonium to the ammonia gas, and a fourth member optionally acts on the ammonia gas. The third member and the fourth member may be such as described above with reference to FIGS. 3C and 3E.

At block 2606, the optoelectronic reader emits a light towards the sensing cartridge. In an embodiment, the optoelectronic reader includes a LED configured to emit the light towards the sensing cartridge.

At block 2608, the optoelectronic reader senses reflected light from the sensing cartridge and provides a measurement based on the reflected light. In an embodiment, the optoelectronic reader includes a sensing photodiode configured to sense the reflected light from the sensing cartridge and to provide a measurement based on the reflected light. In some embodiments, the measurement may correspond to raw measurements, e.g., voltage values, obtained over time. For example, as described above with reference to FIGS. 18, the optoelectronic reader may output a series of voltage values collected over a time period, e.g., 500 seconds. In some embodiments, the measurement may correspond to a change in a measurement, e.g., a voltage change, that occurred over time. For example, as described above with reference to FIGS. 19, the optoelectronic reader may output a voltage change value corresponding to the difference in the voltage measured at an initial time (at or just after time zero) and at 300 seconds.

At block 2610, a processor quantifies the ammonia gas based on the measurement. In an embodiment, the optoelectronic reader includes a processor that is configured to derive a value corresponding to ammonia level. In another embodiment, the optoelectronic reader provides the measurement to a remote processor that is configured to a value corresponding to ammonia level.

In either case, the processor may be configured to derive a value corresponding to ammonia in whole blood based on the measurements, as described above with reference to FIG. 18. For example, a processor may be configured to execute a software application that processes measurements from the optoelectronic reader and outputs a value corresponding to the concentration of ammonia in the whole blood. As previously described, in such an example, a sensing cartridge of the optoelectronic reader contains fitting parameters (or calibration factors). In one embodiment, the fitting parameters are proportional to voltage change measured at 300 s. In another embodiment, the fitting parameters are based on derivatives of raw signals, which are described with reference to FIGS. 18, 21A, and 22.

With reference to FIG. 1, a system 100 for quantifying ammonia gas in whole blood as describe above with reference to FIG. 26 includes a sensing cartridge 104 and an optoelectronic reader 102. The optoelectronic reader 102 is configured to receive and removably couple with the sensing cartridge 104 and to quantify ammonia gas in whole blood based on reflected light from the sensing cartridge or to provide measurements for use in quantifying the ammonia gas. To this end, and with additional reference to FIGS. 2A and 2B, the optoelectronic reader 102 includes a LED 214-1, 214-2 configured to emit a light towards the sensing cartridge 104, and a sensing photodiode 216-1, 216-2 configured to sense reflected light from the sensing cartridge and to provide a measurement based on the reflected light. A processor resident within the optoelectronic reader 102 is configured to quantify the ammonia gas based on the measurement. Alternatively, the optoelectronic reader 102 is configured to communicate the measurement to a processor remote from the optoelectronic reader 102, wherein the remote processor is configured to quantify the ammonia gas based on the measurement. The quantification may be a concentration of ammonia or an amount of ammonia, and may serve as a biomarker for purposes of monitoring patient conditions. To this end, quantifications (or biomarkers) may be obtained periodically, e.g., hourly, daily, weekly, and processed to detect a trend in the biomarker, and to tailor patient therapy accordingly. For example, an ammonia scavenging drug regime (e.g., dosage, frequency of drug intake, etc.) may be adjusted based on a trend in ammonia concentration.

In other embodiments, the reader 102 may be configured to quantify ammonia gas in whole blood or to provide related measurements for use in quantifying ammonia gas in whole blood based on sensing techniques other than optoelectronic. For example, the reader may quantify ammonia gas in whole blood or provide related measurements based on electrochemical sensing by an electrochemical sensor or electrical sensing by an electrode sensor.

With reference to FIG. 3C, the sensing cartridge 300-3 may include a first member set 305-1 having a first member 306-1, a second member 306-2 coupled to the first member, a third member 306-3 coupled to the second member, and a fourth member 306-4 coupled to the third member. The first member 306-1 is configured to separate plasma from whole blood, where the whole blood has a cellular component with a hydrodynamic diameter greater than 0.01 µm. The second member 306-2 is configured to wick the plasma from the whole blood, where the second member acts on ammonium in the plasma to shift a phase equilibrium of the ammonium to ammonia gas. The third member 306-3 is configured to prevent liquid permeation produced by the shift in the phase equilibrium of the ammonium to the ammonia gas. The fourth member 306-4 is configured to act on the ammonia gas.

While the method of FIG. 26 and the system for performing the method are specific to the analysis of whole blood, the method and system are applicable to other body fluid besides whole blood. For example, the method and apparatus may be embodied for the analysis of urine. To this end, a system 100 for quantifying ammonia gas in urine includes a sensing cartridge 104 and an optoelectronic reader 102. The optoelectronic reader 102 is configured to receive and removably couple with the sensing cartridge 104 and to quantify ammonia gas in urine based on reflected light from the sensing cartridge or to provide measurements for use in quantifying the ammonia gas. To this end, and with additional reference to FIGS. 2A and 2B, the optoelectronic reader 102 includes a LED 214-1, 214-2 configured to emit a light towards the sensing cartridge 104, and a sensing photodiode 216-1, 216-2 configured to sense reflected light from the sensing cartridge and to provide a measurement based on the reflected light. A processor resident within the optoelectronic reader 102 is configured to quantify the ammonia gas based on the measurement. Alternatively, the optoelectronic reader 102 is configured to communicate the measurement to a processor remote from the optoelectronic reader 102, wherein the remote processor is configured to quantify the ammonia gas based on the measurement. The quantification may be a concentration of ammonia or an amount of ammonia, and may serve as a biomarker for purposes of monitoring patient conditions. To this end, quantifications (or biomarkers) may be obtained periodically, e.g., hourly, daily, weekly, and processed to detect a trend in the biomarker, and to tailor patient therapy accordingly. For example, an ammonia scavenging drug regime (e.g., dosage, frequency of drug intake, etc.) may be adjusted based on a trend in ammonia concentration.

In other embodiments, the reader 102 may be to quantify ammonia gas in urine or to provide measurements for use in quantifying ammonia gas in urine based on sensing techniques other than optoelectronic. For example, the reader may quantify ammonia gas in urine or provide related measurements based on electrochemical sensing by an electrochemical sensor or electrical sensing by an electrode sensor.

With reference to FIG. 3C, the sensing cartridge 300-3 may include a first member set 305-1 having a first member 306-1, a second member 306-2 coupled to the first member, a third member 306-3 coupled to the second member, and a fourth member 306-4 coupled to the third member. The first member 306-1 is configured to separate supernatant from urine, where the urine has a cellular component with a hydrodynamic diameter greater than 0.01 µm. The second member 306-2 is configured to wick the supernatant from the urine, where the second member acts on ammonium in the supernatant to shift a phase equilibrium of the ammonium to ammonia gas. The third member 306-3 is configured to prevent liquid permeation produced by the shift in the phase equilibrium of the ammonium to the ammonia gas. The fourth member 306-4 is configured to act on the ammonia gas.

In some embodiments, the devices, systems, and/or techniques for deriving a permeate from a feed solution may be used for bicarbonate ion and/or carbonate ion conversion to carbon dioxide gas. In such an embodiment, a phase change occurs in a second member or a third member of a sensing cartridge. The driving force for the phase change is pH. The second member or the third member may be dip coated in an acidic solution (e.g., citric acid) or in a buffer with a pH of 5 or less, and dried at 60° C. for 24 hours. In some embodiments, the carbon dioxide gas is measured using carbon dioxide specific sensing chemistry. In such an embodiment, a three or four layer sensor may be used to measure the carbon dioxide gas. As an example, the three or four layer sensor may include a feed separation layer, a permeate acidification layer, a diffusion layer, and/or a sensing layer. In such an example, the sensing layer has a carbon dioxide sensitive chromogenic indicator embedded into a polymer coated on a transparent substrate. The chromogenic indicator may be m-cresol purple embedded onto a polytetrafluoroethylene support or into a polymer coated onto a transparent substrate. The chromogenic indicator may also be a zeolite imidazolate framework (ZIF) (e.g., a zeolite imidazolate framework-8 (ZIF-8)) embedded in a polymer matrix (e.g., cellulose) on a polyethylene terephthalate (PET) substrate.

In some embodiments, the devices, systems, and/or techniques for deriving a permeate from a feed solution may implement expulsion of a dissolved liquid in the permeate via a temperature swing. The temperature swing may reduce solubility of a gas in the dissolved liquid, resulting in the gas being expelled from the permeate. As an example, dissolved gas (e.g., sulfur dioxide (wastewater)) is expelled from a liquid containing the dissolved gas. In such an example, the dissolved gas is expelled via an increase in temperature of the liquid that causes a decrease in solubility of the dissolved gas. In an embodiment, the feed solution containing dissolved gas is separated by a first member of a sensing cartridge. Then the permeate, still containing the dissolved gas, is heated to a temperature that decreases the solubility of the desired gas in the liquid thus expelling the gas. As an example, a membrane is heated through incorporation of nanophotonic particles and irradiation with light, by being a conductive membrane that is heated by resistive heating or dielectric heating, or by first applying the feed solution and (about one minute later) placing the sensing cartridge in an oven for conductive or convective heating. In some embodiments, the dissolved gas expelled from the feed solution is captured after the temperature swing. In such an embodiment, a system such as a condenser or an adsorption column captures the expelled gas.

Examples of dissolved gases include, sulfur dioxide ($SO_2$), oxygen ($O_2$), ammonia ($NH_3$), argon (Ar), carbon monoxide (CO), carbon dioxide ($CO_2$), chlorine ($Cl_2$), ethane ($C_2H_6$), hydrogen ($H_2$), hydrogen sulfide ($H_2S$), helium (He), methane ($CH_4$), nitrogen ($N_2$), and ethylene ($C_2H_4$). Sulfur dioxide has a solubility of ~110 g of sulfur dioxide gas per kg of water at 20° C. which decreases to <~50 g of sulfur dioxide gas per kg of water at >40° C. Oxygen has a solubility of ~0.041 g of oxygen gas per kg of water at 20° C. which decreases to <~0.022 g of oxygen gas per kg of water at >60° C. Ammonia has a solubility of ~500 g of ammonia gas per kg of water at 20° C. which decreases to <~190 g of ammonia gas per kg of water at >60° C. Argon has a solubility of ~0.59 g of argon gas per kg of water at 20° C. which decreases to <~0.03 g of argon gas per kg of water at >60° C. Carbon monoxide has a solubility of ~0.028 g of carbon monoxide gas per kg of water at 20° C. which decreases to <~0.015 g of carbon monoxide gas per kg of water at >60° C. Carbon dioxide has a solubility of ~1.6 g of carbon dioxide gas per kg of water at 20° C. which decreases to <~0.6 g of carbon dioxide gas per kg of water at >60° C. Chlorine has a solubility of ~7 g of chlorine gas per kg of water at 20° C. which decreases to <~3.2 g of chlorine gas per kg of water at >60° C. Ethane has a solubility of ~0.06 g of ethane gas per kg of water at 20° C. which decreases to <~0.025 g of ethane gas per kg of water at >60° C. Ethylene has a solubility of ~0.13 g of ethylene gas per kg of water at 20° C. which decreases to <~0.12 g of ethylene gas per kg of water at >30° C. Hydrogen has a solubility of ~0.0016 g of hydrogen gas per kg of water at 20° C. which decreases to <~0.00115 g of hydrogen gas per kg of water at >60° C. Hydrogen sulfide has a solubility of ~3.9 g of hydrogen sulfide gas per kg of water at 20° C. which decreases to <~1.5 g of hydrogen sulfide gas per kg of water at >60° C. Helium has a solubility of ~0.0015 g of helium gas per kg of water at 20° C. which decreases to <~0.0013 g of helium gas per kg of water at >60° C. Methane has a solubility of ~0.024 g of methane gas per kg of water at 20° C. which decreases to <~0.0075 g of methane gas per kg of water at >60° C. Nitrogen has a solubility of ~0.0175 g of nitrogen gas per kg of water at 20° C. which decreases to <~0.011 g of nitrogen gas per kg of water at >60° C.

In some embodiments, the devices, systems, and/or techniques for deriving a permeate from a feed solution may measure a dissolved gas in the feed solution through expulsion of the dissolved gas. The dissolved gas may be expelled by altering the solubility of the gas in the feed solution. As an example, increasing the temperature may cause the dissolved gas to expel by decreasing the solubility of the gas in the feed solution. The expelled gas may then be measured using specific sensing chemistry for the expelled gas. In an embodiment, for wastewater containing hydrogen sulfide, the device includes a chromogenic sensing member as a hydrogen sulfide sensing member. The chromogenic sensing member may be, e.g., a transparent support coated with carbon dots on ZIF-8 with terbium ion and guanosine monophosphate on the surface, or modified ZIFs into a polymer on a transparent substrate.

As may be used herein, the term "configured to" indicates that an element includes one or more of components, attachments, circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between devices, components, or members and/or indirect connection between devices, components, or members via an intervening item (e.g., an item includes, but is not limited to, a device, a component, a member, etc.). As may be used herein, the terms "substantially" and "approximately" provide an industry-accepted tolerance for its corresponding term and/or relativity between items.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other similar devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A sensing cartridge comprising:
   a first member comprising an asymmetric membrane having a first surface having a first average pore size and a second surface opposite the first surface having a second average pore size less than the first average pore size;
   a second member having a surface in interfacial contact with the second surface of the first member, wherein the second member has an average pore size greater than the second average pore size at the second surface of the first member;
   a third member; and
   a fourth member,
   wherein:
   the first average pore size of the first member, the second average pore size of the first member, and the average pore size of the second member are relatively sized such that: the first member receives on the first surface, a feed solution comprising a permeate, cellular components in the permeate, and a constituent in the permeate; presents at the second surface, the permeate including the constituent; and retains the cellular components, and the second member wicks the permeate including the constituent through the second surface of the first member,
   the second member is configured to act on the constituent in the permeate to shift a phase equilibrium of the constituent to a gas,
   the third member is between the second member and the fourth member and comprises a hollow ring spacer that separates the second member from the fourth member and allows the gas from the second member to pass through the hollow ring spacer to the fourth member, and
   the fourth member is configured to capture and respond to the gas.

2. The sensing cartridge of claim 1, wherein the second member is one of a woven paper, a non-woven paper, a membrane, a structure of natural fiber, a structure of synthetic fiber, and a porous material.

3. The sensing cartridge of claim 1, wherein the second member includes hydrophobic patterned areas that penetrate through the second member, and wherein the hydrophobic patterned areas exhibit hydrophobic deionized water droplet contact angles.

4. The sensing cartridge of claim 1, wherein the second member includes at least one of an additive and a catalyst.

5. The sensing cartridge of claim 1, wherein the second member includes an additive that induces a shift in a phase equilibrium of the permeate by changing a pH of the permeate to form an alkaline fluid with a pH of at least 8.

6. The sensing cartridge of claim 1, wherein the second member includes an additive that induces a shift in a phase equilibrium of the permeate by changing a pH of the permeate to form an acidic fluid with a pH of at most 6.5.

7. The sensing cartridge of claim 1, wherein:
   each of the first member, the second member, the third member, and the fourth member has a corresponding height, width, length, perimeter, and area, and
   at least one of the corresponding height, width, length, perimeter, and area of each of the second member, the third member, and the fourth member is different from the corresponding height, width, length, perimeter, and area of the first member.

8. The sensing cartridge of claim 1, wherein the fourth member includes a gas responsive layer that has a proportional change in frequency in response to a quantity of gas.

9. The sensing cartridge of claim 1, wherein a zero member is coupled to the first member, and wherein the zero member is configured to enable transport of the feed solution to the first member through a microfluidic structure with a channel diameter of less than 2,000 μm.

10. The sensing cartridge of claim 1, wherein:
    the constituent in the permeate that the second member is configured to act on is one of:
    a dissolved ionic species that is at least one of ammonium ($NH_4^+$), bicarbonate ($HCO_3^-$), carbonate ($CO_3^{2-}$), hemoglobin, carbon monoxide (CO), cyanuric acid (HCN), chloride ($Cl^-$), proton ($H^+$), nitrate ($NO_3^-$), nitrite ($NO_2^-$), arsenite ($AsO_3^{3-}$), arsenate ($AsO_4^{3-}$), and sulfate ($SO_4^2$), and
    a dissolved gas that is at least one of ammonia ($NH_3$), carbon dioxide ($CO_2$), carbon monoxide (CO), cyanuric acid (HCN), chlorine ($Cl_2$), hydrogen ($H_2$), nitrogen dioxide ($NO_2$), nitric oxide (NO), diarsenic trioxide ($As_2O_3$), diarsenic pentaoxide ($As_2O_5$), sulfur dioxide ($SO_2$).

11. A system comprising:
    a sensing cartridge that includes:
    a first member comprising an asymmetric membrane having a first surface having a first average pore size and a second surface opposite the first surface having a second average pore size less than the first average pore size;
    a second member having a surface in interfacial contact with the second surface of the first member, wherein the second member has an average pore size greater than the second average pore size at the second surface of the first member;
    a third member; and
    a fourth member,
    wherein:
    the first average pore size of the first member, the second average pore size of the first member, and the average pore size of the second member are relatively sized such that:
    the first member receives on the first surface, a feed solution comprising a permeate, cellular components in the permeate, and a constituent in the permeate; presents at the second surface, the permeate including the constituent; and retains the cellular components,
    the second member wicks the permeate including the constituent through the second surface of the first member, and
    the second member is configured to shift a phase equilibrium of a constituent in the permeate to a gas,
    the third member is between the second member and the fourth member and comprises a hollow ring spacer that separates the second member from the fourth member and allows the gas from the second member to pass through the hollow ring spacer to the fourth member, and
    the fourth member is configured to capture and respond to the gas; and
    a reader configured to:
    receive and removably couple with the sensing cartridge, and quantify the constituent in the sensing cartridge based on at least one of optical sensing, electrochemical sensing, and electrical sensing.

12. A system comprising:
a sensing cartridge that includes:
- a first member comprising an asymmetric membrane having a first surface having a first average pore size and a second surface opposite the first surface having a second average pore size less than the first average pore size; and; and
- a second member having a surface in interfacial contact with the second surface of the first member, wherein the second member has an average pore size greater than the second average pore size at the second surface of the first member;
- a third member coupled to the second member; and
- a fourth member coupled to the third member;

wherein:
the first average pore size of the first member, the second average pore size of the first member, and the average pore size of the second member are relatively sized such that: the first member receives on the first surface, a feed solution comprising a permeate, cellular components in the permeate, and a constituent in the permeate; presents at the second surface, the permeate including the constituent; and retains the cellular components, and the second member wicks the permeate including the constituent through the second surface of the first member, and the second member is configured to shift a phase equilibrium of a constituent in the permeate to a gas, the third member comprises a hollow ring spacer that separates the second member from the fourth member and allows the gas from the second member to pass through the hollow ring spacer to the fourth member, and the fourth member is configured to respond to the gas; and
an optoelectronic reader that includes:
- a sensing light emitting diode (LED) configured to emit a light towards the sensing cartridge; and
- a sensing photodiode configured to sense reflected light from the sensing cartridge and to provide a measurement based on the reflected light; and
- a processor configured to quantify the constituent based on the measurement.

13. The sensing cartridge of claim 7, wherein:
at least one of the corresponding length and width of the second member is less than the corresponding length and width of the first member, and
at least one of the corresponding length and width of the third member is greater than the corresponding length and width of the second member and less than the corresponding length and width of the first member.

14. The sensing cartridge of claim 1, wherein the first member has a thickness and the second member has a thickness greater than the thickness of the first member.

15. The sensing cartridge of claim 14, wherein the thickness of the second member is between one half the thickness of the first member and 210 μm.

16. The sensing cartridge of claim 14, wherein the thickness of the second member is between 10 μm and 210 μm.

* * * * *